US010285915B2

(12) United States Patent
Sagel et al.

(10) Patent No.: US 10,285,915 B2
(45) Date of Patent: *May 14, 2019

(54) STRIP FOR THE DELIVERY OF AN ORAL CARE ACTIVE AND METHODS FOR APPLYING ORAL CARE ACTIVES

(71) Applicant: The Procter & Gamble Company, Cincinnati, OH (US)

(72) Inventors: Paul Albert Sagel, Maineville, OH (US); Jean Jianqun Zhao, Cincinnati, OH (US); Lan Ngoc Nguyen, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 316 days.

This patent is subject to a terminal disclaimer.

(21) Appl. No.: 14/055,964

(22) Filed: Oct. 17, 2013

(65) Prior Publication Data

US 2014/0178443 A1    Jun. 26, 2014

Related U.S. Application Data

(60) Provisional application No. 61/714,828, filed on Oct. 17, 2012.

(51) Int. Cl.
| | | |
|---|---|---|
| *A61K 8/02* | (2006.01) | |
| *A61K 8/22* | (2006.01) | |
| *A61Q 11/00* | (2006.01) | |
| *A61K 8/42* | (2006.01) | |
| *A61K 8/81* | (2006.01) | |

(52) U.S. Cl.
CPC .......... *A61K 8/0245* (2013.01); *A61K 8/0204* (2013.01); *A61K 8/22* (2013.01); *A61K 8/42* (2013.01); *A61K 8/8111* (2013.01); *A61Q 11/00* (2013.01); *A61K 2800/56* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 1,979,119 | A | 10/1934 | Radzinsky |
| 2,560,724 | A | 7/1951 | Harrison |
| 2,835,628 | A | 5/1958 | Saffir |
| 2,994,362 | A | 8/1961 | Hall |
| 3,047,966 | A | 8/1962 | Greenspan |
| 3,070,102 | A | 12/1962 | Macdonald |
| 3,096,202 | A | 7/1963 | De Groot Von Arx |
| 3,256,014 | A | 6/1966 | Kelsey |
| 3,444,858 | A | 5/1969 | Russell |
| 3,598,123 | A | 8/1971 | Zaffaroni |
| 3,625,215 | A | 12/1971 | Quislilng |
| 3,640,741 | A | 2/1972 | Etes |
| 3,657,413 | A | 4/1972 | Rosenthal et al. |
| 3,659,928 | A | 5/1972 | Macfarlane |
| 3,688,406 | A | 9/1972 | Porter et al. |
| 3,711,182 | A | 1/1973 | Jasgur |
| 3,729,839 | A | 5/1973 | Bourdier |
| 3,754,332 | A | 8/1973 | Warren |
| 3,784,390 | A | 1/1974 | Hijiya et al. |
| 3,844,286 | A | 10/1974 | Cowen |
| 3,859,987 | A | 1/1975 | Holstad |
| 3,902,509 | A | 9/1975 | Tundermann et al. |
| 3,955,281 | A | 5/1976 | Weitzman |
| 3,964,164 | A | 6/1976 | Hesselgren |
| 3,972,995 | A | 8/1976 | Tsuk et al. |
| 3,998,215 | A | 12/1976 | Anderson et al. |
| 4,029,757 | A | 6/1977 | Miodozeniec et al. |
| 4,029,758 | A | 6/1977 | Miodozeniec et al. |
| 4,031,200 | A | 6/1977 | Reif |
| 4,032,627 | A | 6/1977 | Suchan et al. |
| 4,072,551 | A | 2/1978 | Dabal et al. |
| 4,084,700 | A | 4/1978 | Dunchock |
| 4,136,145 | A | 1/1979 | Fuchs et al. |
| 4,136,162 | A | 1/1979 | Fuchs et al. |
| 4,138,314 | A | 2/1979 | Patil et al. |
| 4,138,814 | A | 2/1979 | Weitzman |
| 4,139,627 | A | 2/1979 | Lane et al. |
| 4,182,222 | A | 1/1980 | Stahl |
| 4,211,330 | A | 7/1980 | Strock |
| 4,232,334 | A | 11/1980 | Dyson |
| 4,251,400 | A | 2/1981 | Columbus |
| 4,273,418 | A | 6/1981 | Gillespie et al. |
| 4,292,299 | A | 9/1981 | Suzuki et al. |
| 4,294,820 | A | 10/1981 | Keith et al. |
| 4,307,075 | A | 12/1981 | Martin |
| 4,308,250 | A | 12/1981 | Griffin et al. |
| 4,324,547 | A | 4/1982 | Arcan et al. |
| 4,325,855 | A | 4/1982 | Dickmann et al. |
| 4,331,576 | A | 5/1982 | Colon et al. |
| 4,335,731 | A | 6/1982 | Bora |
| 4,363,843 | A | 12/1982 | Crofts |
| 4,373,036 | A | 2/1983 | Chang et al. |
| 4,376,628 | A | 3/1983 | Aardse |

(Continued)

FOREIGN PATENT DOCUMENTS

| | | |
|---|---|---|
| CA | 681997 | 3/1964 |
| CA | 1209761 | 8/1986 |

(Continued)

OTHER PUBLICATIONS

Ogah, A. O et al., The Effects of Linear Low-Density Polyethylene (LLDPE) on the Mechanical Properties of High-Density Polyehtylene (HDPE) Film Blends, Apr. 2012, International Journal of Engineering and Management Sciences, vol. 3(2), pp. 85-90.*

(Continued)

*Primary Examiner* — Mina Haghighatian
*Assistant Examiner* — Luke E Karpinski
(74) *Attorney, Agent, or Firm* — Parker D. McCrary

(57) ABSTRACT

A strip of material for the delivery of an oral care active is disclosed. The strip of material includes a structural elastic-like film backing layer including a strainable network having a first region and a second region formed of substantially the same material composition, the first region providing a first, elastic-like resistive force to an applied axial elongation, and the second region providing a second distinctive resistive force to further applied axial elongation, thereby providing at least two stages of resistive forces in use; and an oral care composition disposed on the film, the oral care composition including an oral care active.

4 Claims, 23 Drawing Sheets

(56) References Cited

U.S. PATENT DOCUMENTS

| | | | |
|---|---|---|---|
| 4,428,373 A | 1/1984 | Seid et al. |
| 4,431,631 A | 2/1984 | Clipper et al. |
| 4,438,258 A | 3/1984 | Graham |
| 4,442,258 A | 4/1984 | Sunakawa et al. |
| 4,460,562 A | 7/1984 | Keith et al. |
| 4,482,535 A | 11/1984 | Sugar et al. |
| 4,491,479 A | 1/1985 | Lauchenauer et al. |
| 4,503,070 A | 3/1985 | Eby, III |
| 4,515,162 A | 5/1985 | Yamamoto et al. |
| 4,517,173 A | 5/1985 | Kizawa et al. |
| 4,518,721 A | 5/1985 | Dhabhar et al. |
| 4,522,593 A | 6/1985 | Fischer |
| 4,522,805 A | 6/1985 | Gordon |
| 4,522,806 A | 6/1985 | Muhlemann et al. |
| 4,528,180 A | 7/1985 | Schaeffer |
| 4,532,063 A | 7/1985 | Gueldenzopf |
| 4,537,778 A | 8/1985 | Clipper et al. |
| 4,544,354 A | 10/1985 | Gores et al. |
| 4,554,154 A | 11/1985 | White |
| 4,557,692 A | 12/1985 | Chorbajian |
| 4,560,351 A | 12/1985 | Osborne |
| 4,568,536 A | 2/1986 | Kronenthal et al. |
| 4,592,487 A | 6/1986 | Simon et al. |
| 4,592,488 A | 6/1986 | Simon et al. |
| 4,592,726 A | 6/1986 | Brilliant |
| 4,593,053 A | 6/1986 | Jevne et al. |
| 4,623,394 A | 11/1986 | Nakamura et al. |
| 4,640,685 A | 2/1987 | Croll |
| 4,650,665 A | 3/1987 | Kronenthal et al. |
| 4,661,070 A | 4/1987 | Friedman |
| 4,687,663 A | 8/1987 | Schaeffer |
| 4,690,996 A | 9/1987 | Shih et al. |
| 4,696,757 A | 9/1987 | Blank et al. |
| 4,712,460 A | 12/1987 | Allen et al. |
| 4,713,239 A | 12/1987 | Babaian et al. |
| 4,713,243 A | 12/1987 | Schiraldi et al. |
| 4,722,761 A | 2/1988 | Cartmell et al. |
| 4,728,291 A | 3/1988 | Golub |
| 4,741,700 A | 5/1988 | Barabe |
| 4,741,941 A | 5/1988 | Englebert et al. |
| 4,755,385 A | 7/1988 | Etienne et al. |
| 4,755,386 A | 7/1988 | Hsiao et al. |
| 4,765,983 A | 8/1988 | Takayanagi |
| 4,770,634 A | 9/1988 | Pellico et al. |
| 4,772,470 A | 9/1988 | Inoue et al. |
| 4,777,046 A | 10/1988 | Iwakura et al. |
| 4,786,253 A | 11/1988 | Morals |
| 4,788,052 A | 11/1988 | Ng et al. |
| 4,799,888 A | 1/1989 | Golub |
| 4,812,308 A | 3/1989 | Winston et al. |
| 4,828,113 A | 5/1989 | Friedland et al. |
| 4,837,008 A | 6/1989 | Rudy et al. |
| 4,839,156 A | 6/1989 | Ng et al. |
| 4,839,157 A | 6/1989 | Mei-King Ng et al. |
| 4,849,213 A | 7/1989 | Schaeffer |
| 4,849,246 A | 7/1989 | Schmidt |
| 4,851,394 A | 7/1989 | Kubodera et al. |
| 4,860,754 A | 8/1989 | Sharik et al. |
| RE33,093 E | 10/1989 | Schiraldi et al. |
| 4,876,092 A | 10/1989 | Mizobuchi et al. |
| 4,895,517 A | 1/1990 | Fischer |
| 4,895,721 A | 1/1990 | Drucker |
| 4,900,253 A | 1/1990 | Landis |
| 4,900,552 A | 2/1990 | Sanvordeker |
| 4,900,554 A | 2/1990 | Yanagibashi |
| 4,902,227 A | 2/1990 | Smith |
| 4,910,247 A | 3/1990 | Haldar et al. |
| 4,915,950 A | 4/1990 | Miranda et al. |
| 4,919,615 A | 4/1990 | Croll |
| 4,925,670 A | 5/1990 | Schmidt |
| 4,927,634 A | 5/1990 | Sorrentino et al. |
| 4,927,636 A | 5/1990 | Hijiya et al. |
| 4,931,282 A | 6/1990 | Asmus et al. |
| 4,948,580 A | 8/1990 | Browing |
| 4,968,251 A | 11/1990 | Darnell |
| 4,971,782 A | 11/1990 | Rudy et al. |
| 4,972,946 A | 11/1990 | Whittaker |
| 4,978,531 A | 12/1990 | Yamazaki et al. |
| 4,980,152 A | 12/1990 | Frazier et al. |
| 4,983,379 A | 1/1991 | Schaeffer |
| 4,983,381 A | 1/1991 | Zaragoza |
| 4,988,500 A | 1/1991 | Hunter et al. |
| 4,990,089 A | 2/1991 | Munro |
| 5,001,170 A | 3/1991 | Keegan |
| 5,004,631 A | 4/1991 | Humphries et al. |
| 5,024,701 A | 6/1991 | Desmarais |
| 5,047,244 A | 9/1991 | Sanvordeker et al. |
| 5,059,120 A | 10/1991 | Lee |
| 5,059,417 A | 10/1991 | Williams et al. |
| 5,064,717 A | 11/1991 | Suzuki et al. |
| 5,076,791 A | 12/1991 | Madray |
| 5,084,268 A | 1/1992 | Thaler |
| 5,098,303 A | 3/1992 | Fischer |
| 5,122,365 A | 6/1992 | Murayama |
| 5,126,066 A | 6/1992 | Torenbeek et al. |
| 5,137,729 A | 8/1992 | Kuroya et al. |
| 5,158,825 A | 10/1992 | Altwirth |
| 5,160,737 A | 11/1992 | Friedman et al. |
| 5,165,424 A | 11/1992 | Silverman |
| 5,166,233 A | 11/1992 | Kuroya et al. |
| 5,171,564 A | 12/1992 | Nathoo et al. |
| 5,186,938 A | 2/1993 | Sablotsky et al. |
| RE34,196 E | 3/1993 | Munro |
| 5,192,802 A | 3/1993 | Rencher |
| 5,211,559 A | 5/1993 | Hart et al. |
| 5,229,164 A | 7/1993 | Pins et al. |
| 5,234,342 A | 8/1993 | Fischer |
| 5,246,371 A | 9/1993 | Fischer |
| 5,252,334 A | 10/1993 | Chiang et al. |
| 5,256,402 A | 10/1993 | Prencipe et al. |
| 5,271,940 A | 12/1993 | Cleary et al. |
| 5,288,231 A | 2/1994 | Kuehn et al. |
| 5,288,498 A | 2/1994 | Stanley et al. |
| 5,290,566 A | 3/1994 | Schow et al. |
| 5,302,375 A | 4/1994 | Viscio |
| 5,310,563 A | 5/1994 | Curtis et al. |
| 5,314,915 A | 5/1994 | Rencher |
| 5,320,831 A | 6/1994 | Majeti et al. |
| 5,324,342 A | 6/1994 | Mori et al. |
| 5,326,685 A | 7/1994 | Gaglio et al. |
| 5,330,746 A | 7/1994 | Friedman et al. |
| 5,332,576 A | 7/1994 | Mantelle |
| 5,340,314 A | 8/1994 | Tarvis |
| 5,340,581 A | 8/1994 | Tseng et al. |
| 5,344,702 A | 9/1994 | Haubs et al. |
| 5,345,551 A | 10/1994 | Schmidt |
| 5,356,291 A | 10/1994 | Darnell |
| 5,364,267 A | 11/1994 | Fischer |
| 5,376,006 A | 12/1994 | Fischer |
| 5,380,198 A | 1/1995 | Suhonen |
| 5,387,103 A | 2/1995 | Fischer |
| 5,393,528 A | 2/1995 | Staab |
| 5,401,495 A | 3/1995 | Murayama |
| 5,401,528 A | 3/1995 | Schmidt |
| 5,409,631 A | 4/1995 | Fischer |
| 5,425,641 A | 6/1995 | Fischer |
| 5,425,953 A | 6/1995 | Sintov et al. |
| 5,427,770 A | 6/1995 | Viccaro et al. |
| 5,433,952 A | 7/1995 | Sipos et al. |
| 5,438,076 A | 8/1995 | Friedman et al. |
| 5,455,043 A | 10/1995 | Fischel-Ghodsian |
| 5,458,879 A | 10/1995 | Singh et al. |
| 5,462,749 A | 10/1995 | Rencher |
| 5,464,348 A | 11/1995 | Fischer |
| 5,472,704 A | 12/1995 | Santus et al. |
| 5,474,780 A | 12/1995 | Chang |
| 5,505,933 A | 4/1996 | Norfleet et al. |
| 5,509,800 A | 4/1996 | Cunningham |
| 5,522,726 A | 6/1996 | Hodosh |
| 5,529,782 A | 6/1996 | Staab |
| 5,534,562 A | 7/1996 | Fischer |
| 5,560,379 A | 10/1996 | Pieczenik |
| 5,565,190 A | 10/1996 | Santalucia et al. |
| 5,575,654 A | 11/1996 | Fontenot |

(56) References Cited

U.S. PATENT DOCUMENTS

| | | |
|---|---|---|
| 5,575,655 A | 11/1996 | Darnell |
| 5,579,523 A | 11/1996 | Tanaka |
| 5,593,684 A | 1/1997 | Baker et al. |
| 5,599,552 A | 2/1997 | Dunn et al. |
| 5,599,553 A | 2/1997 | Chung |
| 5,603,701 A | 2/1997 | Fischer |
| 5,611,687 A | 3/1997 | Wagner |
| 5,614,174 A | 3/1997 | Hsu et al. |
| 5,616,027 A | 4/1997 | Jacobs |
| 5,618,273 A | 4/1997 | Fischer |
| 5,620,322 A | 4/1997 | Lococo |
| 5,626,866 A | 5/1997 | Ebert et al. |
| 5,629,003 A | 5/1997 | Horstmann et al. |
| 5,631,000 A | 5/1997 | Pellico et al. |
| 5,631,055 A | 5/1997 | Vines et al. |
| 5,635,162 A | 6/1997 | Fischer |
| 5,639,445 A | 6/1997 | Curtis et al. |
| 5,648,064 A | 7/1997 | Gaffar et al. |
| 5,660,178 A | 8/1997 | Kantner et al. |
| 5,662,758 A | 9/1997 | Hamilton et al. |
| 5,678,273 A | 10/1997 | Porcelli |
| 5,683,680 A | 11/1997 | Santalucia et al. |
| 5,685,712 A | 11/1997 | Fischer |
| 5,692,900 A | 12/1997 | Fischer |
| 5,700,148 A | 12/1997 | Fischer |
| 5,700,478 A | 12/1997 | Biegajski et al. |
| 5,707,235 A | 1/1998 | Knutson |
| 5,707,736 A | 1/1998 | Levy et al. |
| 5,708,052 A | 1/1998 | Fischer |
| 5,713,738 A | 2/1998 | Yarborough |
| 5,722,833 A | 3/1998 | Fischer |
| 5,723,132 A | 3/1998 | Tseng et al. |
| 5,725,843 A | 3/1998 | Fischer |
| 5,730,959 A | 3/1998 | Prencipe et al. |
| 5,746,598 A | 5/1998 | Fischer |
| 5,759,037 A | 6/1998 | Fischer |
| 5,759,038 A | 6/1998 | Fischer |
| 5,766,011 A | 6/1998 | Sibner |
| 5,770,105 A | 6/1998 | Fischer |
| 5,770,182 A | 6/1998 | Fischer |
| 5,770,219 A | 6/1998 | Chiang et al. |
| 5,780,045 A | 7/1998 | Mcquinn et al. |
| 5,785,955 A | 7/1998 | Fischer |
| 5,788,579 A | 8/1998 | Cherry et al. |
| 5,789,465 A | 8/1998 | Harvey et al. |
| 5,800,832 A | 9/1998 | Tapolsky et al. |
| 5,816,804 A | 10/1998 | Fischer |
| 5,819,765 A | 10/1998 | Mittiga |
| 5,820,854 A | 10/1998 | Glandorf |
| 5,827,525 A | 10/1998 | Liao et al. |
| 5,827,591 A | 10/1998 | Blok et al. |
| 5,846,058 A | 12/1998 | Fischer |
| 5,851,512 A | 12/1998 | Fischer |
| 5,851,551 A | 12/1998 | Tseng et al. |
| 5,855,870 A | 1/1999 | Fischer |
| 5,858,332 A | 1/1999 | Jensen et al. |
| 5,860,809 A | 1/1999 | Meehan |
| 5,863,202 A | 1/1999 | Fontenot et al. |
| 5,871,607 A | 2/1999 | Hamilton et al. |
| 5,879,591 A | 3/1999 | Nagoh et al. |
| 5,879,691 A | 3/1999 | Sagel et al. |
| 5,888,480 A | 3/1999 | Homola et al. |
| 5,891,453 A | 4/1999 | Sagel et al. |
| 5,894,017 A | 4/1999 | Sagel et al. |
| 5,922,307 A | 7/1999 | Montgomery |
| 5,953,885 A | 9/1999 | Berman et al. |
| 5,965,235 A | 10/1999 | McGuire et al. |
| 5,968,633 A | 10/1999 | Hamilton et al. |
| 5,980,249 A | 11/1999 | Fontenot |
| 5,980,868 A | 11/1999 | Homola et al. |
| 5,985,249 A | 11/1999 | Fischer |
| 5,989,569 A | 11/1999 | Dirksing et al. |
| 6,030,222 A | 2/2000 | Tarver |
| 6,036,943 A | 3/2000 | Fischer |
| 6,045,811 A | 4/2000 | Dirksing et al. |
| 6,083,421 A | 7/2000 | Huang et al. |
| 6,086,855 A | 7/2000 | Fischer |
| 6,094,889 A | 8/2000 | Van Loon et al. |
| 6,096,328 A | 8/2000 | Sagel et al. |
| 6,099,940 A | 8/2000 | Hamilton et al. |
| 6,106,293 A | 8/2000 | Wiesel |
| 6,126,443 A | 10/2000 | Burgio |
| 6,136,297 A | 10/2000 | Sagel et al. |
| 6,142,780 A | 11/2000 | Burgio |
| 6,155,825 A | 12/2000 | Fischer |
| 6,155,832 A | 12/2000 | Wiesel |
| 6,182,420 B1 | 2/2001 | Berman et al. |
| 6,183,251 B1 | 2/2001 | Fischer |
| 6,194,062 B1 | 2/2001 | Hamilton et al. |
| 6,197,331 B1 | 3/2001 | Lerner et al. |
| 6,217,335 B1 | 4/2001 | Riitan |
| 6,234,793 B1 | 5/2001 | Fischer |
| 6,254,965 B1 | 7/2001 | McGuire et al. |
| 6,274,122 B1 | 8/2001 | Mclaughlin |
| 6,277,458 B1 | 8/2001 | Dirksing et al. |
| 6,287,120 B1 | 9/2001 | Wiesel |
| 6,306,206 B1 | 10/2001 | Fischer |
| 6,306,370 B1 | 10/2001 | Jensen |
| 6,309,625 B1 | 10/2001 | Jensen |
| 6,322,360 B1 | 11/2001 | Burgio |
| 6,343,932 B1 | 2/2002 | Wiesel |
| 6,361,844 B1 | 3/2002 | Ou-Yang et al. |
| 6,368,576 B1 | 4/2002 | Fischer |
| 6,379,155 B1 | 4/2002 | Riitano |
| 6,391,283 B1 | 5/2002 | Jensen |
| 6,402,514 B1 | 5/2002 | Fischer |
| 6,400,801 B1 | 6/2002 | Fischer |
| 6,461,158 B1 | 10/2002 | Sagel et al. |
| 6,468,079 B1 | 10/2002 | Fischer |
| 6,500,004 B2 | 12/2002 | Jensen |
| 6,527,751 B2 | 3/2003 | Fischer |
| 6,514,483 B2 | 4/2003 | Xu et al. |
| 6,551,579 B2 | 4/2003 | Sagel |
| 6,582,708 B1 | 6/2003 | Sagel |
| 6,625,839 B2 | 9/2003 | Fischer |
| 6,649,147 B1 | 11/2003 | Ye et al. |
| 6,652,282 B2 | 11/2003 | Jensen |
| 6,729,879 B2 | 5/2004 | Allred |
| 6,746,664 B2 | 6/2004 | Allred |
| 6,756,417 B2 | 6/2004 | Allred |
| 6,814,794 B2 | 11/2004 | Allred |
| 6,860,736 B2 | 3/2005 | Allred |
| 6,884,426 B2 | 4/2005 | Sagel |
| 6,916,463 B2 | 7/2005 | Lee et al. |
| 6,949,240 B2 | 9/2005 | Sagel |
| 6,981,874 B2 | 1/2006 | Allred |
| 6,994,546 B2 | 2/2006 | Fischer |
| 6,997,706 B2 | 2/2006 | Jessop |
| 6,997,708 B2 | 2/2006 | Allred |
| 7,011,523 B2 | 3/2006 | Allred |
| 7,018,622 B2 | 3/2006 | Goodhart |
| 7,040,893 B2 | 5/2006 | Fischer |
| 7,040,897 B2 | 5/2006 | Fischer |
| 7,048,543 B2 | 5/2006 | Allred |
| 7,052,275 B2 | 5/2006 | Allred |
| 7,056,118 B2 | 6/2006 | Allred |
| 7,059,857 B2 | 6/2006 | Allred |
| 7,059,858 B2 | 6/2006 | Mclean |
| 7,074,042 B2 | 7/2006 | Allred |
| 7,094,393 B2 | 8/2006 | Montgomery |
| 7,097,449 B2 | 8/2006 | Jessop |
| 7,121,828 B2 | 10/2006 | Fischer |
| 7,122,199 B2 | 10/2006 | Sagel |
| 7,128,899 B2 | 10/2006 | Chen |
| 7,144,250 B2 | 12/2006 | Fischer |
| 7,168,951 B2 | 1/2007 | Fischer |
| 7,172,423 B2 | 2/2007 | Allred |
| 7,192,276 B2 | 3/2007 | Fischer |
| 7,192,280 B2 | 3/2007 | Allred |
| 7,198,619 B2 | 4/2007 | Fischer |
| 7,198,623 B2 | 4/2007 | Fischer |
| 7,264,471 B2 | 9/2007 | Malcmacher |
| 7,320,598 B2 | 1/2008 | Jensen |
| 7,398,598 B2 | 7/2008 | Lewis |

(56) References Cited

U.S. PATENT DOCUMENTS

| | | | |
|---|---|---|---|
| 7,534,264 | B2 | 5/2009 | Fischer |
| 7,780,449 | B2 | 8/2010 | Fischer |
| 7,862,801 | B2 | 1/2011 | Chen |
| 7,862,802 | B2 | 1/2011 | Kim |
| 8,524,200 | B2 | 9/2013 | Sagel |
| 2001/0009755 | A1 | 7/2001 | Fischer |
| 2002/0006387 | A1 | 1/2002 | Sagel et al. |
| 2002/0018754 | A1 | 2/2002 | Sagel |
| 2002/0146666 | A1 | 10/2002 | Sagel et al. |
| 2003/0145863 | A1 | 8/2003 | Allred |
| 2003/0147258 | A1 | 8/2003 | Fischer |
| 2003/0148242 | A1 | 8/2003 | Fischer |
| 2003/0156980 | A1 | 8/2003 | Fischer |
| 2003/0199605 | A1 | 10/2003 | Fischer |
| 2003/0211056 | A1 | 11/2003 | Sagel et al. |
| 2003/0215766 | A1 | 11/2003 | Fischer |
| 2004/0120903 | A1 | 6/2004 | Sagel |
| 2004/0122377 | A1 | 6/2004 | Fischer |
| 2004/0214130 | A1 | 10/2004 | Fischer |
| 2004/0214131 | A1 | 10/2004 | Fischer |
| 2004/0214140 | A1 | 10/2004 | Fischer |
| 2004/0249016 | A1 | 12/2004 | Allred |
| 2005/0016884 | A1 | 1/2005 | Stout |
| 2005/0019277 | A1 | 1/2005 | Sagel |
| 2005/0064371 | A1 | 3/2005 | Soukos |
| 2005/0069837 | A1 | 3/2005 | Lewis |
| 2005/0130096 | A1 | 6/2005 | Stout |
| 2005/0136373 | A1 | 6/2005 | Fischer |
| 2005/0238591 | A1 | 10/2005 | Sagel |
| 2005/0249680 | A1 | 11/2005 | Goodhart |
| 2005/0287086 | A1 | 12/2005 | Sagel |
| 2007/0003495 | A1 | 1/2007 | Sagel |
| 2007/0086961 | A1 | 4/2007 | Sagel |

FOREIGN PATENT DOCUMENTS

| | | |
|---|---|---|
| CA | 2078960 | 10/1993 |
| CA | 2095445 | 7/1995 |
| CA | 2000040 | 10/1995 |
| DE | 1104116 | 4/1961 |
| DE | 2330869 | 1/1975 |
| EP | 0 252 459 | 1/1988 |
| EP | 0 328 317 A1 | 8/1989 |
| EP | 0 637 446 A1 | 2/1995 |
| FR | 2637 175 | 4/1990 |
| FR | 2701397 | 2/1998 |
| GB | 1240411 | 7/1971 |
| GB | 2108841 | 5/1983 |
| GB | 2 115 431 A | 9/1983 |
| GB | 2159052 | 11/1985 |
| IE | 42604 | 9/1980 |
| JP | 57-028102 | 2/1982 |
| JP | 58-213709 A | 12/1983 |
| JP | 60 005159 A | 1/1985 |
| JP | 60 005160 A | 1/1985 |
| JP | 61-280423 | 12/1986 |
| JP | 62-142113 A | 6/1987 |
| JP | 62-255417 A | 11/1987 |
| JP | 63 005756 | 1/1988 |
| JP | 63-054318 A | 3/1988 |
| JP | 10-040423 | 2/1989 |
| JP | 12-79838 | 11/1989 |
| JP | 03-264522 A | 3/1990 |
| JP | 02-202814 A | 8/1990 |
| JP | 02-250826 A | 10/1990 |
| JP | 03-198754 | 8/1991 |
| JP | 32-64522 | 11/1991 |
| JP | 32-64523 | 11/1991 |
| JP | 05-124954 | 5/1993 |
| JP | 06-321744 A | 5/1993 |
| JP | 05-220203 A2 | 8/1993 |
| JP | 05-236885 | 9/1993 |
| JP | 07-100186 | 4/1995 |
| JP | 08-183732 | 7/1996 |
| JP | 08-325128 | 12/1996 |
| JP | 10-017448 A | 1/1998 |
| JP | 10-226639 | 8/1998 |
| RU | 2075965 C1 | 9/1994 |
| WO | WO19 88/06879 | 9/1988 |
| WO | WO 1989/10740 | 11/1989 |
| WO | WO 1991/06289 | 5/1991 |
| WO | WO 1991/16041 | 10/1991 |
| WO | WO 1995/17158 | 6/1995 |
| WO | WO 1996/25910 | 8/1996 |
| WO | WO 1998/17263 | 4/1998 |
| WO | WO 1998/55044 | 12/1998 |
| WO | WO 1999/027895 | 6/1999 |
| WO | WO 2003/015656 A2 | 2/2003 |
| WO | WO 2005/058266 A1 | 6/2005 |

OTHER PUBLICATIONS

International Search Report and Written Opinion for PCT/US2013/065365 dated Nov. 14, 2014.
3M Dental Products 2000 Product Catalog 32 pgs.
Besner, et al, Practical Endodontics, 1994, pp. 7-15, 178-180, Mosby-Year Book, Inc.
J.H. Briston, "Plastic Films", 1974, pp. 96-97.
James W. Curtis, et al, "Assessing the effects of 10 percent carbamide peroxide on oral soft tissues", *JADA*, 1996, vol. 127, pp. 1218-1223.
Claudia Paula Drew, "Teeth Bleaching . . . a Vital technique for you to know", Sep./Oct. 1988, pp. 23-25.
R.E. Goldstein, et al., "Chemistry of Bleaching", *Complete Dental Bleaching*, 1995, pp. 25-32 & 90-97, Quintessence Publishing Co, Inc.
Van B. Haywood, et al., "Nightguard Vital Bleaching", *Quintessence International*, 1989, vol. 20, No. 3, pp. 173-176, 19th International Meeting on Dental Implants and Transplants, Bologna, Italy.
Van B. Haywood, "History, Safety, and Effectiveness of Current Bleaching Techniques and Applications of the Nightguard Vital Bleaching Technique", *Quintessence International*, 1992, vol. 23, No. 7, pp. 471-488.
Van B. Haywood, "Nightguard Vital Bleaching", *Dentistry Today*, 1997, pp. 86-91.
Van B. Haywood, "Nightguard Vital Bleaching: Current Concepts and Research", *JADA*, 1997, vol. 128, pp. 19S-25S.
Van B. Haywood, et al, "Nightguard vital bleaching: how safe is it?", *Esthetic Dentistry*, 1991, vol. 22, No. 7, pp. 515-523.
Van B. Haywood, "Bleaching of vital and nonvital teeth", *Periodontology and Restorative Dentistry*, 1992, pp. 142-149.
Van B. Haywood, "Nightguard vital bleaching, a history and products update: Part 1", *Esthestic Dentistry Update*, 1991, vol. 2, No. 4, pp. 63-66.
Van Benjamin Haywood, "Overview and Status of Mouthguard Bleaching" *Journal of Esthetic Dentistry*, 1991, vol. 3,No. 5, pp. 157-161.
Van B. Haywood, "Nightguard vital bleaching: current information and research", *Esthetic Dentistry Update*, 1990, vol. 1, No. 2, pp. 20-25.
"Tooth Bleaching, Home-Use Products", *Clinical Research Associates Newsletter*, 1989, pp. 1-4.
Van B. Haywood, "The food and drug administration and its influence on home bleaching", *ADA*, 1993, pp. 12-18.
Van B. Haywood, "Efficacy of foam liner in 10% carbamide peroxide bleaching technique", *Esthetic Dentistry*, 1993, vol. 24, No. 9, pp. 663-666.
Van B. Haywood, "Response of normal and tetracycline-stained teeth with pulp-size variation to nightguard vital bleaching", *Journal of Esthetic Dentistry*, 1994, vol. 6, No. 3, pp. 109-114.
Van B. Haywood, "Historical development of whiteners: clinical safety and efficacy", *Aesthetics*, 1997, pp. 98-104.
Van B. Haywood, "Considerations and variations of dentist-prescribed,home-applied vital tooth-bleaching techniques", *Compend Continu Educ Dent*, 1994, Suppl.No. 17, pp. s616-s621.
Van B. Haywood, "Effectiveness, side effects and long-term status of nightguard vital bleaching", *JADA*, 1994, vol. 125, pp. 1219-1226.

(56) References Cited

OTHER PUBLICATIONS

Van B. Haywood, "Commonly asked questions about nightguard vital bleaching", *IDA Journal*, 1993, pp. 28-33.
Van B. Haywood, "Commonly asked questions about nightguard vital bleaching", *The Dental Assistant*, Mar./Apr. 1996, pp. 6-12.
Van B. Haywood, "Efficacy of six months of nightguard vital bleaching of tetracycline-stained teeth", *Journal of Esthetic Dentistry*, 1997, vol. 9, No. 1, pp. 13-19.
Van B. Haywood, "Achieving, maintaining and recovering successful tooth bleaching", Journal of Esthetic Dentistry, 1996, vol. 8, No. 1, pp. 31-38.
Ralph H. Leonard, et al, "Salivary pH changes during 10% carbamide peroxide bleaching" *Dental Research*, 1994, vol. 25, No. 8, pp. 547-550.
Ralph H. Leonard, et al, "Change in pH of plaque and 10% carbamide peroxide solution during nightguard vial bleaching treatment" *Esthetic Dentistry*, 1994, vol. 25, No. 12, pp. 819-823.
Ralph H. Leonard Jr., et al, "Risk factors for developing tooth sensitivity and gingival irritation associated with nightguard vital bleaching", *Esthetic Dentistry*, 1997, vol. 28,No. 8, pp. 527-534.
M.S. McCRACKEN, "Demineralization effects of 10 percent carbamide peroxide", *Journal of Dentistry*, 1996, vol. 24, No. 6, pp. 395-398.
G. McLaughlin, et al., "Materials" and "Clinical Techniques", *Color Atlas of Tooth Whitening*, 1991, pp. 35-38 & 45-50, Ishiyaku EuroAmerica, Inc.
S.M. Newman, et al., "Tray-Forming Technique for Dentist-Supervised Home Bleaching", *Quintessence International*, 1995, pp. 447-453, vol. 26, No. 7.
Sue Ellen Richardson, "Home bleaching: effectiveness, history, technique, bleaches, cost and safety" *The Journal of the Greater Houston Dental Society*, 1989, pp. 22-26.
Fonda G. Robinson, et al, "Effect of 10 percent carbamide peroxide on color of provisional restoration materials", *JADA*, 1997, vol. 128, pp. 727-731.
Carl M. Russell, et al, "Dentist-supervised home bleaching with ten percent carbamide peroxide gel: a six month study", *Journal of Esthetic Dentistry*, 1996, vol. 8, No. 4, pp. 177-182.
Carolyn F. G. Wilson, et al, "Color change following vital bleaching of tetracycline-stained teeth" *Pediatric Dentistry*, 1985, vol. 7, No. 3, pp. 205-208.
Christopher J. Woolverton, "Toxicity of two carbamide peroxide products used in nightguard vital bleaching", *American Journal of Dentistry*, 1993, vol. 6, No. 6, pp. 310-314.
"Tooth Bleaching, Home-Use Products", *Clinical Research Associates Newsletter*, 1989, vol. 3, Issue 12.
Office Action from the USPTO, dated Sep. 5, 2002, issued on U.S. Appl. No. 09/864,686, filed May 24, 2001, assignee—The Procter & Gamble Co., now abandoned.
Office Action from the USPTO, dated May 28, 2003, issued on U.S. Appl. No. 09/864,686, filed May 24, 2001, assignee—The Procter & Gamble Company, now abandoned.
Messing, J.J. et al., Color Atlas of Endodontics, 1988, pp. 106-107, 135-140, 173-175, 257-259; The C.V. Mosby Company, Ltd.
Kunio, Y., et al., "Bandage for Application in Oral Cavity", JP 3-264523 abstract; Nov. 25, 1991.
Sumiko, K., et al., "Bandage for Oral Application", JP 2250826 abstract; Oct. 8, 1990.
Encyclopedia of Chemical Technology, vol. 19, Fourth Edition, pp. 712-715.
Press Release, Colgate-Palmolive (India) Limited :: Pressroom, http://www.colgate.co.in/pressroom/030917.shtm, pp. 1-2.
Product Advertisement GNPD/Whitening Gel, Colgate Simply White, http://www.gnpd.com/sinatra/gnpd&lang=uk/search/results&selection=pg&page=1&mode . . . , p. 1.
International Search Report and Written Report for 6711R dated Sep. 24, 1998.

\* cited by examiner

No Stretch    25% Stretch    50% Stretch    100% Stretch

STRIP FOR THE DELIVERY OF AN ORAL CARE ACTIVE AND METHODS FOR APPLYING ORAL CARE ACTIVES

FIELD OF THE INVENTION

The present disclosure relates to a strip of material for delivery of an oral care active and to methods for applying oral care actives to the desired region of a user's mouth. More particularly, the present disclosure relates to an extensible or stretchable strip of material and optionally a release liner. Such systems and methods can be used, for example, for whitening teeth.

BACKGROUND OF THE INVENTION

Tooth whitening and other at-home and in-office oral care procedures have become popular in today's culture. In the office tooth bleaching generally involves several visits to the dentist and the use of a rubber dam to protect the patient's gums from the bleaching agents. Out of the office tooth bleaching generally involves the use of a device or tray which is made in the dental office to fit the patient's teeth. The device is reused, and therefore, must be sufficiently sturdy to endure repeat handling, cleaning, filling, installation, and wearing. Typically, a patient uses the device in time periods when social contact can be avoided.

Non-professional programs are also available to persons interested in whitening their teeth using commercial products available in stores. The commercial products often provide a kit which includes a generic appliance and a container of bleaching gel. The obvious appeal is the lower cost of the program. A major disadvantage of this generic "one size fits all" appliance is the greater void space between the interior walls of the appliance and the teeth versus a professionally fitted appliance. Hence, in order to insure intimate contact of the bleaching gel and the teeth surfaces, more bleaching gel is required. Furthermore, the poorer fit means a greater loss of bleaching gel onto the gums, into the oral cavity, and eventual ingestion. Since generic appliances are not fitted to the individual user, they are even more bulky in the mouth than the fitted appliances and thus they restrict social discourse during use.

A recognized consumer need is a low cost commercial oral care delivery system that is comfortable to wear that can deliver a sufficient amount of an oral care substance. In addition, a delivery system is needed which does not require extensive user placement manipulation to be certain of good contact for optimal delivery. Furthermore, what is needed is a non-bulky active containment means that will permit the wearer to use the system during social discourse without interfering with the wearer's speech or appearance. Also needed is a containment means that will protect oral care substance from erosion from contact with other oral surfaces and, or saliva.

To address the need, at least with regard to out of the office tooth whitening, whitening strips were developed. Exemplary strip delivery systems and methods of using the strips are disclosed in U.S. Pat. Nos. 6,551,579 B2 and 7,122,199 B2, both to Sagel et al. and assigned to The Procter & Gamble Company, the disclosure of which is incorporated herein by reference. However, there is still a need for improvement as the known strips do not easily provide for customization for different sized users. As such, also needed is a delivery system that is customizable in length, i.e. stretchable, to allow a user to cover the desired number of teeth, without the negative side effects that a user would experience with an elastic material, such as, a pulling force or creeping. Further, there is a need to provide even better and more secure fit for strip-like delivery systems and/or to provide the user with feedback associated with the fit of the device while being worn.

SUMMARY OF THE INVENTION

In one embodiment, a strip of material for the delivery of an oral care active is provided. The strip of material includes a structural elastic-like film backing layer including a strainable network having a first region and a second region formed of substantially the same material composition, the first region providing a first, elastic-like resistive force to an applied axial elongation, and the second region providing a second distinctive resistive force to further applied axial elongation, thereby providing at least two stages of resistive forces in use; and an oral care composition disposed on the film, the oral care composition including an oral care active.

In another embodiment, a stretchable tooth treatment product is provided. The stretchable tooth treatment product includes a structural elastic-like film backing layer, having an average thickness of from about 0.1 mil to about 5.0 mil, the film including: from about 50% to about 90%, by weight of the film, of high-density polyethylene; and from about 10% to about 50%, by weight of the film, of linear low-density polyethylene; and an oral care composition disposed on the film, the oral care composition including: from about 50% to about 99.9%, by weight of the composition, of an adhesive polymer; and from about 0.1% to about 50%, by weight of the composition, of an oral care active.

In another embodiment, a stretchable tooth treatment product is provided. The stretchable tooth treatment product includes a backing layer; and an oral care composition disposed on the backing layer, the oral care composition including an oral care active. The stretchable tooth treatment product exhibits a Young's Modulus of less than about 50 MPa, a strain at break of at least about 250%, and a strain at yield of at least about 30%.

In another embodiment, a method of delivering an oral care active to a plurality of adjacent teeth is provided. The method includes providing a strip of material having a backing layer and an oral care composition disposed on the backing layer, the oral care composition including an oral care active, the strip of material exhibiting a Young's Modulus of less than about 50 MPa, a strain at break of at least about 250%, and a strain at yield of at least about 30%; adjusting the size of the strip of material so that the strip is of a sufficient size to individually fit a wearer's plurality of adjacent teeth when placed against the teeth; and applying the strip of material to the plurality of adjacent teeth.

In another embodiment, a stretchable tooth treatment product is provided. The stretchable tooth treatment product includes a backing layer; and an oral care composition disposed on the backing layer, the oral care composition including an oral care active. The stretchable tooth treatment product exhibits a Young's Modulus of less than about 50 MPa, an initial peel force of greater than about 0.05 N, and less than about 0.05 g of material remaining after an initial peel test as measured according to a Strip Removal Test.

In yet another embodiment, a method of delivering an oral care active to a plurality of adjacent teeth is provided. The method includes providing a strip of material having a backing layer and an oral care composition disposed on the backing layer, the oral care composition including an oral care active, the strip of material exhibiting a Young's Modulus of less than about 50 MPa, an initial peel force of greater than about 0.05 N, and less than about 0.05 g of material remaining after an initial peel test as measured according to a Strip Removal Test; adjusting the size of the strip of material so that the strip is of a sufficient size to individually fit a wearer's plurality of adjacent teeth when placed against the teeth; and applying the strip of material to the plurality of adjacent teeth.

These and other features, aspects and advantages of specific embodiments will become evident to those skilled in the art from a reading of the present disclosure.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
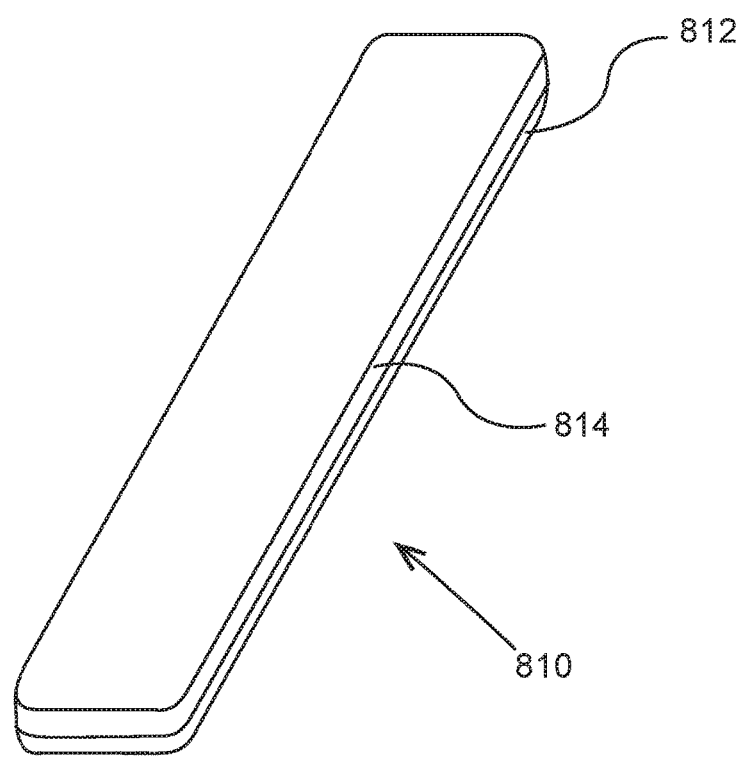
FIG. 1 is a perspective view of one embodiment of a strip of material including a backing layer and an oral care composition disposed thereon according to one or more embodiments illustrated and described herein.

The abbreviation "cm", as used herein, means centimeter. The abbreviation "mm", as used herein, means millimeter.

As used herein, the term "necked backing layer", refers to a backing layer for a strip of material which has been constricted in at least one dimension by applying a tensioning force in a direction that is perpendicular to the desired direction of neck-down.

As used herein, the term "percent neckdown", refers to the ratio determined by measuring the difference between the un-necked dimension and the stabilized necked dimensions of the backing layer in the direction of necking, and then dividing that difference by the un-necked dimension of the backing layer, then multiplying by 100.

Strip of Material

The oral active delivery device may be referred to as a strip of material, a strip or any other suitable name. None of these terms, however, is intended to limit the delivery device to any particular size, shape, composition, material, number of layers, thickness or other characteristic. Rather, the term strip is intended to generally refer to a length of material used to deliver an oral care active to a portion of the user's mouth.

The strip may have a shape that is adapted to fit a user's teeth. The strip may be designed to cover any one or more teeth. For example, the strip may substantially cover the front side of at least a user's front four teeth and two canine teeth or may cover more or fewer teeth when used. By substantially, it is meant that at least half of the front tooth surface is covered. The strip may cover all of the front tooth surface and may also cover portions of the gums adjacent to the teeth. For tooth whitening strips, the strip will generally begin coverage at the point where the surface of the teeth intersect the gums and extend from there away from the gums to cover all or a portion of the individual tooth surfaces.

The strip may be foldable over the tips and onto the back sides of one or more of the teeth. In certain embodiments, the shape of the strip will allow for canine tips to not be covered. By folding over the tips it is meant that the strip covers or wraps around the front side of the tooth over the tip and onto the back side of the tooth. Depending upon the size of the strip, the entire back side of the tooth including the adjacent gum may be covered or only a portion of the back side of the tooth.

The shape of the strip may be any shape which allows it to fit the user and work for the desired purpose. For example, the strip may be substantially trapezoidal in shape. The term substantially trapezoidal is used to mean any shape having four general sides where there are two sides which are generally parallel. This may result from many shapes, including where one side is convex and the opposing side is concave. The arched shape may help to reduce bunching of the strip and allow the strip to lay smoother along the surfaces of the teeth. The strip may be substantially rectangular in shape. This is used generally to mean a shape with four sides which each of two sides are close to parallel. Parallel is used broadly to include when sides are arched, not straight, and generally not perpendicular. Alternatively, the strip may be of any shape such as round or oval. The strip may also be of a shape with any numbers of sides. The shape of the strip does not need to be symmetrical, but can be if desired.

Any of the sides or edges of the strip may be notched, stair stepped, or arched. By notched it is meant that there is a recess, indentation, or curve of some type. By stair stepped it is meant that the side is not straight and may contain one or more stair steps. The strip may also contain slits, cross-slits, holes, perforations, or any suitable formation that allows for the canines to protrude through or be avoided by the strip of material.

Each strip may include a fold line. The fold line is defined as the part of the strip where the tips of the teeth meet the strip when the strip is folded or wrapped over the tips. This line may be from the point where one recess, stair step, or notch on one side extends into the strip the farthest to where the other recess, stair step, or notch extends into the strip the farthest on the opposing side. The fold line will generally extend from one side of the strip to another parallel side and along the longer part of the strip. The fold line may be self adjusting depending upon the size and shape of the strip. With a trapezoidal shape strip, the fold line will be determined based upon the positioning of the strip on a user's teeth.

The strip may have rounded corners. "Rounded corners" is defined as not having any sharp angles or points. The size of the strip can be any suitable size and may be designed to address many different factors, including the number of teeth to be bleached, the size of the teeth, and personal preference of the wearer. In general, the length of the strip is from about 2 cm to about 12 cm, but can be from about 3 cm to about 10 cm, from about 4 cm to about 6 cm or any desired length. If the strip is stair stepped on the sides or trapezoidal shaped, the longer side of the strip of material may be from about 3 cm to about 12 cm, from about 3.1 to about 10 cm, from about 3.5 cm to about 8 cm, from about 4 cm to about 8 cm or any other suitable length. The shorter side may be from about 0.1 cm to about 12 cm, from about 0.5 cm to about 8 cm, from about 1 cm to about 5 cm, from about 1.5 cm to about 3 cm or any other suitable size. The width of the strip of material will also depend upon many factors, including whether or not the strip of material wraps completely around the teeth and covers part or all of the front and back surfaces of the tooth. The width can be any suitable measurement, but has been found to work well in certain embodiments when from about 0.5 cm to about 4 cm or from about 1 cm to about 2 cm.

One or more layers of the strip may comprise materials such as polymers, natural and synthetic wovens, non-wovens, foil, paper, rubber, and combinations thereof. The layers, if any, may include one or more materials. The strip may be substantially water impermeable, permeable and/or dissolvable. The strip may include any materials with the desired flexural rigidity and compatibility with the actives to be used. The materials may comprise a single polymer or a mixtures of polymers. Suitable polymers include, but are not limited to, polyethylene, polypropylene, polyvinylacetate, polyethyl-vinylacetate, polyethyl-vinyl alcohol, polyurethane, polyesters such as Mylar® manufactured by DuPont, fluoroplastics such as Teflon® manufactured by DuPont, biodegradable polymers, renewable polymers, and combinations thereof. The strip has been found to be especially suitable when less than about 1 mm thick, less than about 0.5 mm thick, and more from about 0.001 to about 0.3 mm thick although other thicknesses are possible.

Flexural stiffness is a material property that is a function of a combination of thickness, width, and material modulus of elasticity. The following is a test method for measuring the rigidity of the strip of material. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In one embodiment, the strip of material has a flexural stiffness of less than about 5 grams/cm as measured on a Handle-O-Meter, model #211-300, available from Thwing-Albert Instrument Co. of Philadelphia, Pa., as per test method ASTM D2923-95. The strip of material may have a flexural stiffness less than about 4 grams/cm, less than about 3 grams/cm, or from about 0.1 grams/cm to about 1 grams/cm. Generally, it is desired that the flexural stiffness of the material is substantially constant and does not significantly change during normal use. For example, it may be desirable that the strip not need to be hydrated for the strip to achieve the low flexural stiffness in the above-specified ranges.

This relatively low stiffness enables the strip to drape over the contoured surfaces of teeth with very little force being exerted. That is, conformity to the curvature of the wearer's mouth and gaps between adjacent teeth is maintained because there is little residual force within strip of material to cause it to return to its substantially flat shape. The flexibility of the strip enables the strip of material to contact adjoining soft tissue over an extended period of time without physical irritation. The strip does not require pressure forming it against the teeth.

The strip is held in place on a plurality of adjacent teeth at least partially by an adhesive composition discussed in more detail below. The viscosity and general tackiness of the adhesive composition cause the strip of material to be adhesively attached to a plurality of adjacent teeth without substantial slippage under the potential friction from the lips, tongue, and other soft tissue rubbing against the backing layer during mouth movements associated with talking, drinking, etc. However, this adhesion to the teeth is low enough to allow the strip to be easily removed by the wearer by peeling off the strip using one's finger or fingernail. The strip is easily removable from the surfaces of the teeth without the use of an instrument, a chemical solvent, or undue friction. Chemical solvents include any organic solvents commonly used in oral care products such as alcohol and other safe solvents such as water, which could be used to dilute the gelling agent. Undue friction is described as any type of rubbing with one's finger or a soft implement, such as cotton balls, swabs, or gauze pads.

A peel force of from about 1 gram to about 1500 grams for a 1.5 cm strip width (approximately 1000 grams/cm) is all that is required in certain embodiments. The peel force may be from about 5 grams to about 1250 grams or from about 10 grams to about 1000 grams. The low peel force is desired for consumer handling purposes. The low peel force may be made possible by a non-aggressive gel substance. This works especially well when the flexural stiffness of the strip is low. The adhesion of a stiffer strip would have to be greater in proportion to the strip stiffness in order to prevent the strip from returning to its flat condition and pulling away from the contoured surface of a plurality of teeth.

Referring now to the drawings, and more particularly to FIG. 1, there is shown one embodiment, which is generally indicated as 810. Embodiment 810 represents a strip of material. The strip of material 810 generally may comprise a backing layer 812 and an adhesive composition 814. In another embodiment, the strip of material may also include a release liner.

Figure 2:
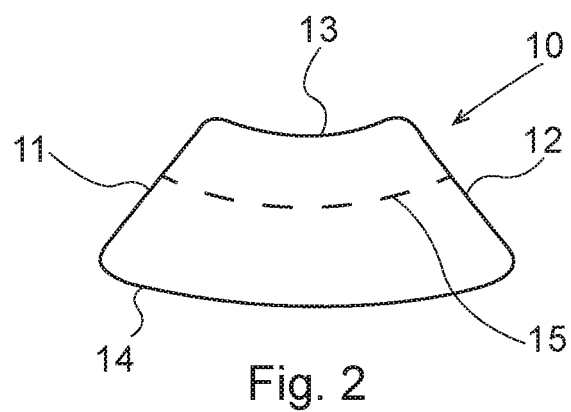
FIG. 2 is a planar view of a strip of material which is substantially trapezoidal in shape according to one or more embodiments illustrated and described herein.

As shown in FIG. 2, in one embodiment, strip of material 10 may be substantially trapezoidal in shape. In one embodiment, strip 10 has a first side 11 and second side 12, a third side 13, and a fourth side 14. First side 11 and second side 12 may have straight sides which angle in from the fourth side 14 to the third side 13. Third side 13 may be concave and shorter then the fourth side 14. The fourth side 14 may be convex. The fourth side 14 may be placed close to the bottom edge of the front side of a user's bottom set of front teeth. Alternatively, if the strip is worn on the user's top set of teeth, the fourth side 14 may be placed along the top part of the front side of a user's top set of front teeth. A fold line 15 of embodiment 10 extends from first side 11 to second side 12. The fold line 15 may be located closer to the third side 13 or the fourth side 14. The fold line 15 may be determined by the size of the user's teeth and the placement of the strip on the user's teeth. The third side 13 may be along the back side of a user's teeth after the strip 10 is folded along the fold line 15.

Figure 3:
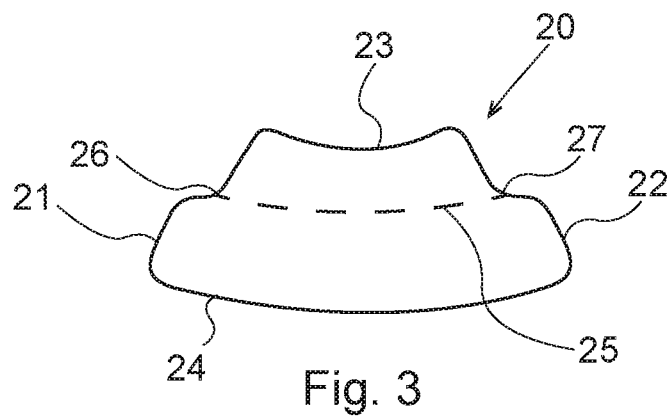
FIG. 3 is a planar view of a strip of material which is substantially trapezoidal in shape with stair stepped sides according to one or more embodiments illustrated and described herein.

As shown in FIG. 3, one embodiment 20 may be substantially trapezoidal in shape with stair stepped sides. Embodiment 20 has a first side 21, a second side 22, a third side 23, and a fourth side 24. Third side 23 may be concave and shorter then the fourth side 24. The fourth side 24 may be convex. First side 21 and second side 22 may be stair stepped sides. Fold line 15 extends from the corners 26 and 27 of the stair step in the first side 21 and the second side 22, respectively. Embodiment 20 can alternatively be described as two substantially trapezoidal shapes placed on top of one another. The top trapezoid is formed by the third side 23, the second side 22 from its corner 27 up to the third side 23, the fold line 25, and the first side 21 from its corner 26 up to the third side 23. The bottom trapezoid is formed by the fold line 25, the second side 22 from its corner 27 down to the fourth side 24, the fourth side 24, and the first side 21 from its corner 26 down to the fourth side 24.

Figure 4:
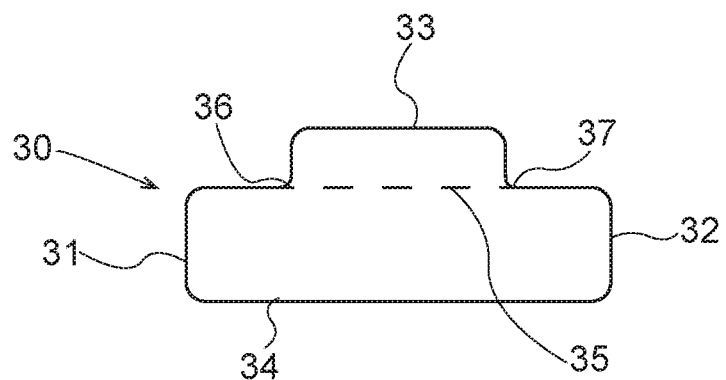
FIG. 4 is a planar view of a strip which is substantially rectangular in shape with stair stepped sides according to one or more embodiments illustrated and described herein.

FIG. 4 illustrates an alternative embodiment 30. The strip of material may be substantially rectangular in shape with stair stepped sides. Embodiment 30 has a first side 31 and second side 32, a third side 33, and a fourth side 34. First side 31 and second side 32 may be both stair stepped sides. Fold line 35 may extend from the corners 36 and 37 of the stair step in the first side 31 and the second side 32, respectively. Embodiment 30 can also be described as two rectangles placed on top of one another. The top rectangle may eb formed by the third side 33, the second side 32 from its corner 37 up to the third side 33, the fold line 35, and the first side 31 from its corner 36 up to the third side 33. This top rectangle may alternatively be described as a flap which fits over the back sides of the user's teeth. The bottom rectangle is formed by the fold line 35, the second side 32 from its corner 37 down to the fourth side 34, the fourth side 34, and the first side 31 from its corner 36 down to the fourth side 34.

The fold line 35 will usually be placed over the tips of a user's teeth enabling the strip to fold down onto both the front side and the back side of the user's teeth. The strip may be placed so that the user's two canine teeth are just outside of corners 36 and 37. The fourth side 34 may be located close to the bottom edge of the front side of a user's bottom set of front teeth. Alternatively if the strip is worn on the user's top set of teeth, the fourth side 34 may be placed along the top part of the front side of a user's top set of front teeth. The third side 33 may be along the back side of a user's teeth.

Figure 5:
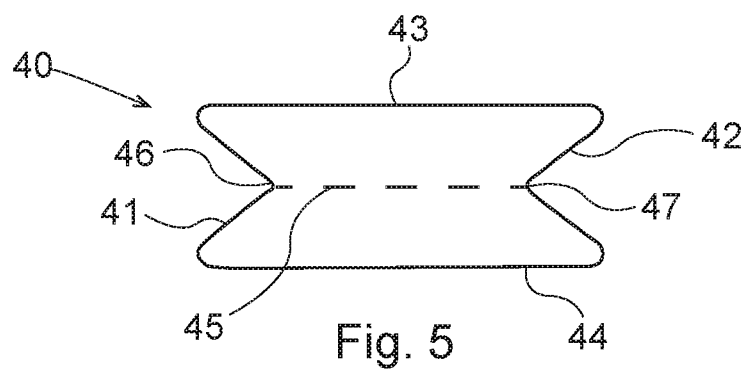
FIG. 5 is a planar view of a strip which is substantially rectangular in shape with notched sides according to one or more embodiments illustrated and described herein.

FIG. 5 details a strip of material substantially rectangular in shape with notched sides. Embodiment 40 has a first side 41, second side 42, a third side 43, and a fourth side 44. Third side 43 and fourth side 44 may be both substantially straight sides and the same length. In one embodiment, first side 41 and second side 42 have notches 46 and 47, respectively, which enable the tips of the canine teeth not to be covered when the strip is placed on the user's teeth. Fold line 45 extends from notch 46 in the first side 41 to notch 47 in the second side 42. Notches 46 and 47 may have a sideways V shapes as shown. The notches may be of any shape including rectangular, semi circles, etc. that allows the tips of the canine teeth to not be wrapped by embodiment 40.

Figure 6:
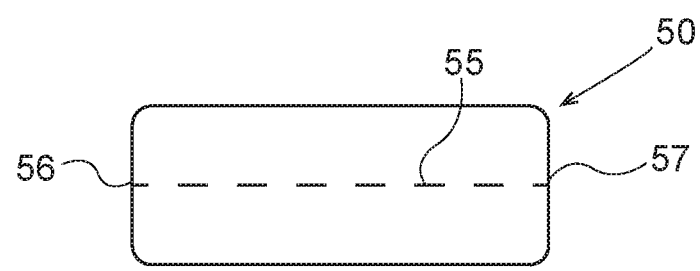
FIG. 6 is a planar view of a strip which is rectangular in shape with two slits according to one or more embodiments illustrated and described herein.
Figure 7:
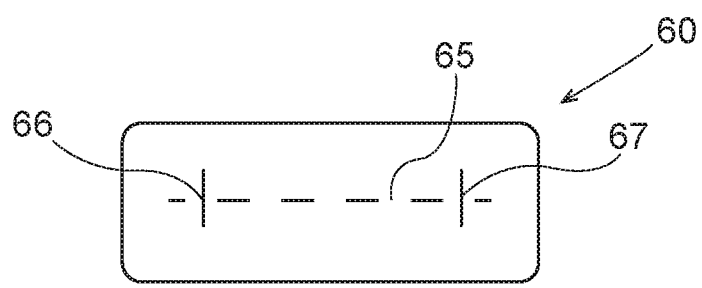
FIG. 7 is a planar view of a strip which is rectangular in shape with two cross-slits according to one or more embodiments illustrated and described herein.
Figure 8:
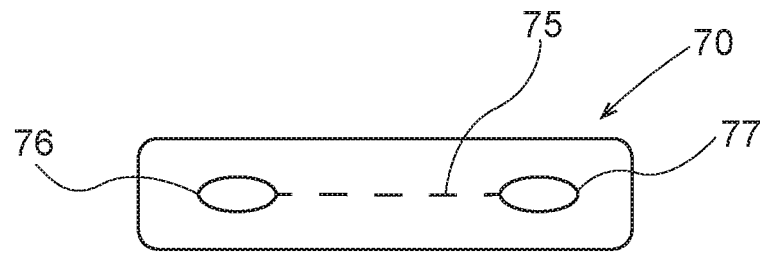
FIG. 8 is a planar view of a strip which is rectangular in shape with two holes according to one or more embodiments illustrated and described herein.

Embodiments 50, 60, and 70 are illustrated by FIGS. 6, 7, and 8 respectively. The strip of material of embodiments 50, 60, and 70 is substantially rectangular in shape with rounded corners. Each embodiment contains two recesses which allow for protrusion of the canine teeth when the strip is placed on a user's teeth. FIG. 6 illustrates where the recesses are straight slits 56 and 57. Slits 56 and 57 extend from the outside edge of embodiment 50 to an interior point. Fold line 55 extends between slits 56 and 57. FIG. 7 shows slits 66 and 67 which are cross-slits. Cross-slits 66 and 67 are located within embodiment 60. Fold line 65 extends from cross-slit 66 to cross-slit 67. Embodiment 70 of FIG. 8 illustrates holes 76 and 77 in the strip. Holes 76 and 77 may be of any size that is sufficient for the tips of the canines to protrude. Fold line 75 extends between holes 76 and 77.

Figure 9:
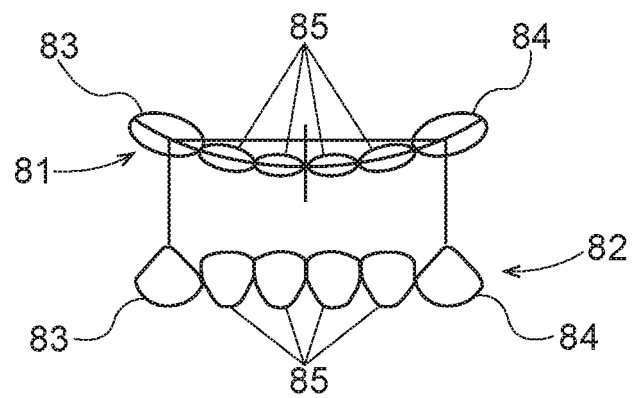
FIG. 9 is a cross-sectional view of a user's front six teeth according to one or more embodiments illustrated and described herein.

FIG. 9 shows corresponding top 81 and front 82 view of a user's bottom set of the front six teeth. Top view 81 illustrates the general arched shape found in the front six teeth. The two canine teeth 83 and 84 are located on opposite sides of the four front teeth 85. Not shown are additional back teeth, such as molars, which are located next to each of the canine teeth. Front view 82 illustrates the general shapes, including the tips, of the front four teeth 85 and canine teeth 83 and 84.

Figure 10:
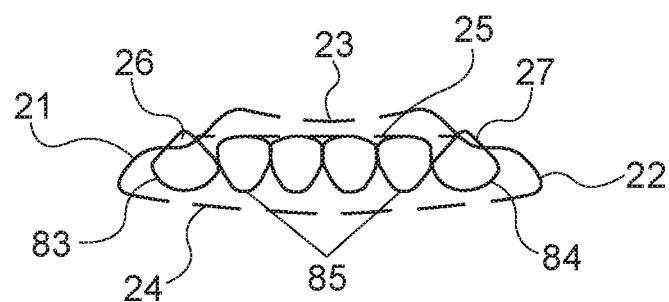
FIG. 10 is cross-sectional view of a strip placed upon a user's front six teeth before being folded over the back sides of the user's teeth according to one or more embodiments illustrated and described herein.

FIG. 10 shows front view 82 of a user's front six teeth shown in FIG. 8 with the strip illustrated by embodiment 20 of FIG. 3. Embodiment 20 is shown placed along the teeth but not yet folded over the teeth. As illustrated, fourth side 24 is placed along the bottom portions of the front four teeth 85 and the two canine teeth 83 and 84. Fold line 25 hits at the tips of the front four teeth 85 and allows the tips of the canine teeth 83 and 84 to be exposed. Canine teeth 83 and 84 protrude at the corners 26 and 27 of the stair steps. Third side 23 will subsequently be folded down onto the back side of the four front teeth 85.

Backing Layer

As noted above, the strip may include one or more layers of the same or different materials. In certain embodiments, the strip includes a backing layer. The backing layer may serve as a protective barrier to prevent, substantially prevent or reduce the amount of saliva contacting the oral care substance and leaching and/or erosion of the substance from the surface of the teeth by the wearer's lips, tongue, and other soft tissue. For some uses, it may be desirable for the substance to act upon the surface of tooth over an extended period of time, from several minutes to several hours. Thus, influencing or controlling leaching and/or erosion may be desirable.

The backing layer may be formed by several of the film making processes known in the art. The backing layer may be a polyethylene made by a blown process or a cast process. Processes, such as extrusion and other processes are also feasible.

While the backing layer may be constructed from a number of different extensible materials as are known in the art, the backing layer, for performance and cost reasons, in one example, may be constructed of a structural elastic-like film (SELF) web. The term "web" herein refers to a sheet-like material comprising a single layer of material or a laminate of two or more layers. In other embodiments, additional formation means for deforming a backing layer into a three-dimensional structure may be used, for example, ring-rolling, "micro-SELF" and "rotary knife aperturing" (RKA).

Each of the four formation means disclosed herein are disclosed as comprising a pair of inter-meshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, while the disclosure of four formation means is illustrated herein, other known formation technologies, such as creping, necking/consolidation, corrugating, embossing, button break, hot pin punching, and the like may also be used. The formation processes known as ring-rolling, micro-SELF and RKA are further disclosed in U.S. Patent Publication No. 2008/0217809, which is hereby incorporated by reference herein.

Figure 11:
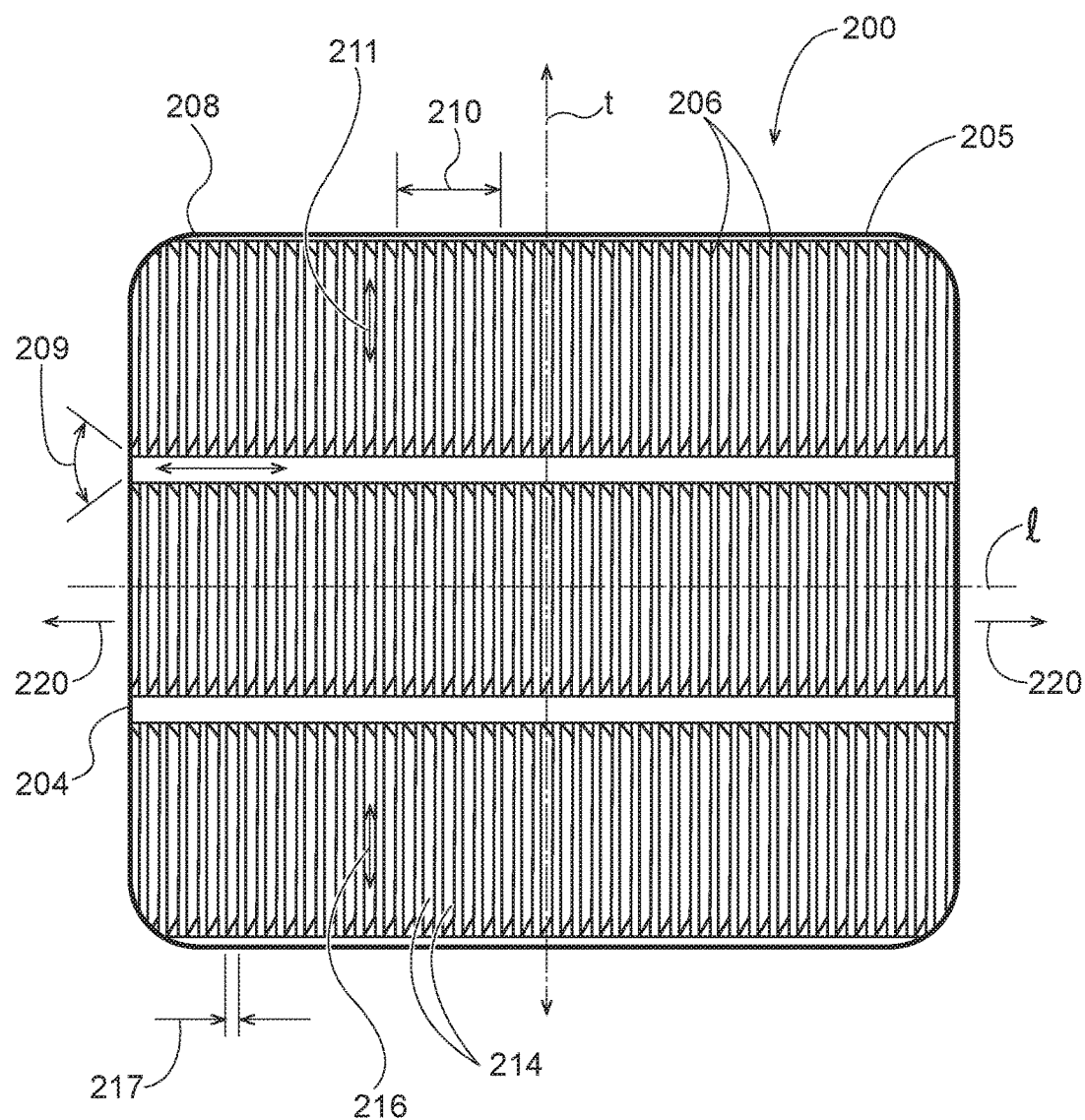
FIG. 11 is a plan view of a SELF web/backing layer having a strainable network according to one or more embodiments illustrated and described herein.

The first formation means for deforming a backing layer in accordance with the present disclosure is a process commonly referred to as "SELF" or "SELF'ing" process. FIG. 11 shows one embodiment of a SELF web 200 of the present disclosure constructed of a single layer of a formed polymeric material. The SELF web 200 is shown in its untensioned condition. The web has two centerlines, a longitudinal centerline, l, and a transverse or lateral centerline, t, which is generally perpendicular to the longitudinal centerline. In one embodiment, the web may be comprised substantially of linear low density polyethylene (LLDPE) although it may also be comprised of other polyolefins such as polyethylenes including low density polyethylene (LDPE), ultra low density polyethylene (ULDPE), high density polyethylene (HDPE) or polypropylene and/or blends thereof of the above and other materials. Examples of other suitable polymeric materials include, but are not limited to, polyester, polyurethanes, compostable or biodegradable polymers, and breathable polymers.

The mass density of high-density polyethylene can range from about 0.93 to about 0.97 $g/cm^3$. Although the density of HDPE is only marginally higher than that of LDPE, HDPE has little branching, giving it stronger intermolecular forces and tensile strength than LDPE. The difference in strength exceeds the difference in density, giving HDPE a higher specific strength. It is also harder and more opaque and can withstand somewhat higher temperatures (120° C./248° F. for short periods, 110° C./230° F. continuously). HDPE, unlike polypropylene, cannot withstand normally-required autoclaving conditions. The lack of branching is ensured by an appropriate choice of catalyst (e.g., Ziegler-Natta catalysts) and reaction conditions. HDPE contains the chemical elements carbon and hydrogen.

LDPE is defined by a density range of from about 0.910 to about 0.940 g/cm³. It is not reactive at room temperatures, except by strong oxidizing agents, and some solvents cause swelling. It can withstand temperatures of 80° C. continuously and 95° C. for a short time. Made in translucent or opaque variations, it is quite flexible, and tough but breakable. LDPE has more branching (on about 2% of the carbon atoms) than HDPE, so its intermolecular forces (instantaneous-dipole induced-dipole attraction) are weaker, its tensile strength is lower, and its resilience is higher. Also, since its molecules are less tightly packed and less crystalline because of the side branches, its density is lower. LDPE contains the chemical elements carbon and hydrogen.

LLDPE is a substantially linear polymer (polyethylene), with significant numbers of short branches, commonly made by copolymerization of ethylene with longer-chain olefins. LLDPE differs structurally from conventional LDPE because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces an LLDPE polymer that has a narrower molecular weight distribution than conventional LDPE and in combination with the linear structure, significantly different rheological properties.

In another embodiment, the web may comprise an extensible polymer at a temperature of from about 0 degrees C. to about 50 degrees C. Extensible polymers include, but are not limited to, polymeric materials that have a percent elongation/strain at break higher than about 50% in the machine direction, and in another embodiment, to having a percent elongation/strain at break higher than about 100% and a Young's Modulus less than about 2,500 MPa in the machine direction, in yet another embodiment, having a percent elongation/strain at break higher than about 100% and a Young's Modulus less than about 2,000 MPa in the machine direction, in yet another embodiment, having a percent elongation/strain at break higher than about 100% and a Young's Modulus less than about 1,000 MPa in the machine direction, and in yet another embodiment, having a percent elongation/strain at break higher than about 100% and a Young's Modulus less than about 500 MPa in the machine direction.

The percent elongation/strain at break is the amount of stretch the film underwent before the point of break. Young's Modulus and percent elongation/strain at break can be measured on a tensile test machine using ASTM standard test method D 882—Tensile Testing of Thin Plastic Sheeting.

Examples of backing layer compositions according to the present disclosure are shown in Table 1.

TABLE 1

Backing Layer Compositions (weight percent)

| Example No. | HDPE Grade | (%) | LLDPE Grade | (%) | Thickness (mil) | Young's Modulus* (MPa) | Strain @ Break % |
|---|---|---|---|---|---|---|---|
| 1 | Equistar L5005 | 90 | Exxon L1001.32 | 10 | 0.35 | 1494 | 154 |
| 2 | Equistar L5005 | 90 | LyondellBasell GA501022 | 10 | 1.10 | 495 | 458 |
| 3 | Equistar L5005 | 90 | LyondellBasell GA501023 | 10 | 0.70 | 587 | 345 |
| 4 | Equistar L5005 | 90 | LyondellBasell GA501024 | 10 | 0.35 | 981 | 251 |
| 5 | Equistar L5005 | 80 | LyondellBasell GA501025 | 20 | 1.10 | 397 | 478 |
| 6 | Equistar L5005 | 80 | LyondellBasell GA501026 | 20 | 0.70 | 486 | 385 |
| 7 | Equistar L5005 | 80 | LyondellBasell GA501027 | 20 | 0.35 | 688 | 254 |
| 8 | Equistar L5005 | 70 | LyondellBasell GA501028 | 30 | 1.10 | 362 | 485 |
| 9 | Equistar L5005 | 70 | LyondellBasell GA501029 | 30 | 0.7 | 381 | 365 |
| 10 | Equistar L5005 | 70 | LyondellBasell GA501030 | 30 | 0.35 | 654 | 255 |
| 11 | Equistar L5005 | 60 | LyondellBasell GA501031 | 40 | 0.7 | 377 | 404 |
| 12 | Equistar L5005 | 60 | LyondellBasell GA501032 | 40 | 0.35 | 544 | 254 |
| 13 | Equistar L5005 | 50 | LyondellBasell GA501033 | 50 | 0.7 | 280 | 415 |
| 14 | Equistar L5005 | 50 | LyondellBasell GA501034 | 50 | 0.35 | 460 | 249 |
| 15 | Equistar L5005 | 70 | Exxon L3001.32 | 30 | 0.7 | 478 | 488 |

*Machine Direction

Figure 11A:
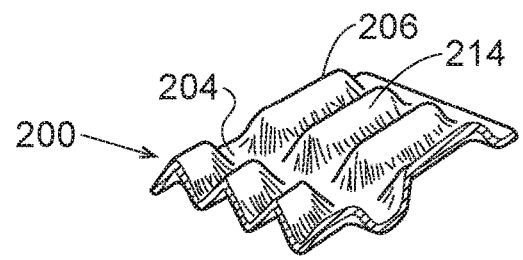
FIG. 11A is a segmented, perspective illustration of the SELF web/backing layer of FIG. 11 in an untensioned condition.

Referring to FIGS. 11 and 11A, the SELF web includes a "strainable network" of distinct regions. As used herein, the term "strainable network" refers to an interconnected and interrelated group of regions which are able to be extended to some useful degree in a predetermined direction providing the SELF web with an elastic-like behavior in response to an applied and subsequently released elongation. The strainable network includes at least a first region 204 and a second region 206. The SELF web 200 includes a transitional region 205 which is at the interface between the first region 204 and the to second region 206. The transitional region 205 will similarly exhibit complex combinations of behavior of both the first region and the second region. It is recognized that the various embodiments will have transitional regions, however, the present disclosure is largely defined by the behavior of the web material in the distinctive regions (for example, first region 204 and second region 206). Therefore, the ensuing description of the present disclosure will be concerned with the behavior of the web material in the first regions and the second regions only since it is not significantly dependent upon the complex behavior of the web material in the transitional regions 205.

SELF web 200 has a first surface and an opposing second surface. In one embodiment, as shown in FIGS. 11 and 11A, the strainable network includes a plurality of first regions 204 and a plurality of second regions 206. The first regions 204 have a first axis 208 and a second axis 209, wherein the first axis 208 may be longer than the second axis 209. The first axis 208 of the first region 204 is substantially parallel to the longitudinal axis of the SELF web 200 while the second axis 209 is substantially parallel to the transverse axis of the SELF web 200. In one embodiment, the second axis of the first region, (i.e., the width of the first region), is from about 0.01 inches to about 0.5 inches, and in another embodiment, from about 0.03 inches to about 0.25 inches. The second regions 206 have a first axis 210 and a second axis 211. The first axis 210 is substantially parallel to the longitudinal axis of the SELF web 200, while the second axis 211 is substantially parallel to the transverse axis of the SELF web 200. In another embodiment, the second axis of the second region, (i.e., the width of the second region), is from about 0.01 inches to about 2.0 inches, and in another embodiment, from about 0.125 inches to about 1.0 inches. In the embodiment of FIG. 11, the first regions 204 and the second regions 206 are substantially linear, extending continuously in a direction substantially parallel to the longitudinal axis of the SELF web 200.

The first region 204 has an elastic modulus E1 and a cross-sectional area A1. The second region 206 has an elastic modulus E2 and a cross-sectional area A2.

In the illustrated embodiment, a portion of the SELF web 200 has been "formed" such that the SELF web 200 exhibits a resistive force along an axis, which in the case of the illustrated embodiment is substantially parallel to the longitudinal axis of the SELF web, when subjected to an applied axial elongation in a direction substantially parallel to the longitudinal axis. As used herein, the term "formed" refers to the creation of a desired structure or geometry upon the SELF web that will substantially retain the desired structure or geometry when it is not subjected to any externally applied elongations or forces, i.e. regions of formation. A SELF web of the present disclosure is comprised of at least a first region and a second region, wherein the first region is visually distinct from the second region. As used herein, the term "visually distinct" refers to features of the SELF web material which are readily discernible to the normal naked eye when the SELF web material or objects embodying these SELF web material are subjected to normal use.

Methods for forming SELF web materials include, but are not limited to, embossing by mating plates or rolls, thermoforming, high pressure hydraulic forming, or casting. While the entire portion of the SELF web 200 has been subjected to a forming operation, the present disclosure may also include subjecting to formation only a portion thereof, for example, a portion of a backing layer.

In one embodiment shown in FIGS. 11 and 11A, the first regions 204 are substantially planar. That is, the material within the first region 204 is in substantially the same condition before and after the formation step undergone by the SELF web 200. The second regions 206 include a plurality of raised rib-like elements 214. The rib-like elements 214 may be embossed, debossed or a combination thereof. The rib-like elements 214 have a first or major axis 216 which is substantially parallel to the transverse axis of the SELF web 200 and a second or minor axis 217 which is substantially parallel to the longitudinal axis of the SELF web 200. The first axis 216 of the rib-like elements 214 is at least equal to, and in one example, longer than the second axis 217. In one embodiment, the ratio of lengths of the first axis 216 to the second axis 217 is at least about 1:1, or greater, and in another embodiment, at least about 2:1 or greater.

The rib-like elements 214 in the second region 216 may be separated from one another by unformed areas, essentially unembossed or debossed, or simply formed as spacing areas. In one embodiment, the rib-like elements 214 are adjacent one another and are separated by an unformed area of less than 0.10 inches as measured perpendicular to the major axis 216 of the rib-like element 214, and in one embodiment, the rib-like element 214 are contiguous having no unformed areas between them.

What makes the SELF web particularly well suited for use as a delivery system including a strip of material is that it exhibits a modified "Poisson lateral contraction effect" substantially less than that of an otherwise identical unformed base web of similar material composition. As used herein, the term "Poisson lateral contraction effect" describes the lateral contraction behavior of a backing material which is being subjected to an applied elongation. The Poisson's Lateral Contraction Effect (PLCE) is calculated using the following formula:

$$PLCE = \frac{\frac{|w2 - w1|}{w1}}{\frac{|l2 - l1|}{l1}}$$

Where w2=The width of the sample under an applied longitudinal elongation
w1=The original width of the sample.
l2=The length of the sample under an applied longitudinal elongation
l1=The original length of the sample (gage length)

In one embodiment, the Poisson lateral contraction effect of the SELF web of the present disclosure is less than about 0.8 when the SELF web is subjected to about 25% elongation. In another embodiment, the SELF web exhibits a Poisson lateral contraction effect less than about 1.0 when the SELF web is subjected to about 50 or even 100% elongation. The Poisson lateral contraction effect of the strips of the present disclosure is determined by the amount of the web material which is occupied by the first and second regions, respectively. As the area of the SELF web material occupied by the first region increases, the Poisson lateral contraction effect also increases. Conversely, as the area of the SELF web material occupied by the second region increases the Poisson lateral contraction effect decreases. In one embodiment, the percent area of the SELF web material occupied by the first region is from about 2% to about 90%, and in another embodiment, from about 5% to about 50%.

Web materials of the prior art which have at least one layer of an elastomeric material will generally have a large Poisson lateral contraction effect, i.e., they will "neck down" as they elongate in response to an applied force. SELF web materials of the present disclosure can be designed to moderate if not substantially eliminate the Poisson lateral contraction effect.

Figure 11B:
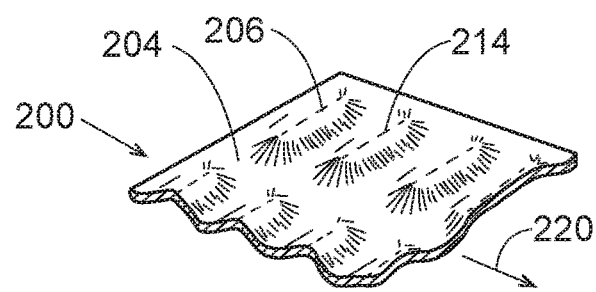
FIG. 11B is a segmented, perspective illustration of the SELF web/backing layer of FIG. 11 in a tensioned condition.
Figure 11C:
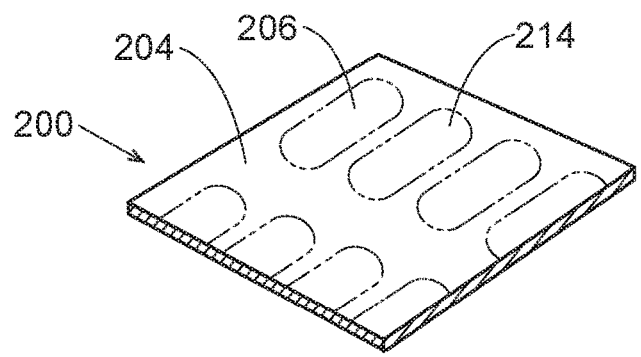
FIG. 11C is a segmented, perspective illustration of the SELF web/backing layer of FIG. 11 in a tensioned condition.

For the SELF web 200, the direction of applied axial elongation, D, indicated by arrows 220 in FIG. 11, is substantially perpendicular to the first axis 216 of the rib-like elements 214, The rib-like elements 214 are able to unbend or geometrically deform in a direction substantially perpendicular to their first axis 216 to allow extension in the SELF web 200, Referring now to FIG. 11B, as the SELF web is subjected to an applied axial elongation, D, indicated by arrows 220 in FIG. 11. The rib-like elements 214 in the second region 206 are experiencing geometric deformation, or unbending, and offer minimal resistance to the applied elongation. As seen in FIG. 11C, the rib-like elements 214 in the second region 206 have become substantially aligned with the axis of applied elongation (i.e., the second region has reached its limit of geometric deformation) and begin to resist further elongation via molecular-level deformation.

When the SELF web is subjected to an applied elongation, the SELF web exhibits an elastic-like behavior as it extends in the direction of applied elongation and returns to its substantially untensioned condition once the applied elongation is removed, unless the SELF web is extended beyond the point of yielding. The SELF web is able to undergo multiple cycles of applied elongation without losing its ability to substantially recover. Accordingly, the SELF web is able to return to its substantially untensioned condition once the applied elongation or force is removed.

While the SELF web may be easily and reversibly extended in the direction of applied axial elongation, in a direction substantially perpendicular to the first axis of the rib-like elements, the SELF web is not as easily extended in a direction substantially parallel to the first axis of the rib-like elements. The formation of the rib-like elements allows the rib-like elements to geometrically deform in a direction substantially perpendicular to the first or major axis of the rib-like elements, while requiring substantially molecular-level deformation to extend in a direction substantially parallel to the first axis of the rib-like elements.

The amount of applied force required to extend the SELF web is dependent upon the composition and cross-sectional area of the web material forming the SELF web and the width and spacing of the first regions, with narrower and more widely spaced first regions requiring lower applied extension forces to achieve the desired elongation. The first axis, (i.e., the length) of the first regions may be greater than the second axis, (i.e., the width) of the first region with a length to width ratio of from about 5:1 or greater.

Figure 12:
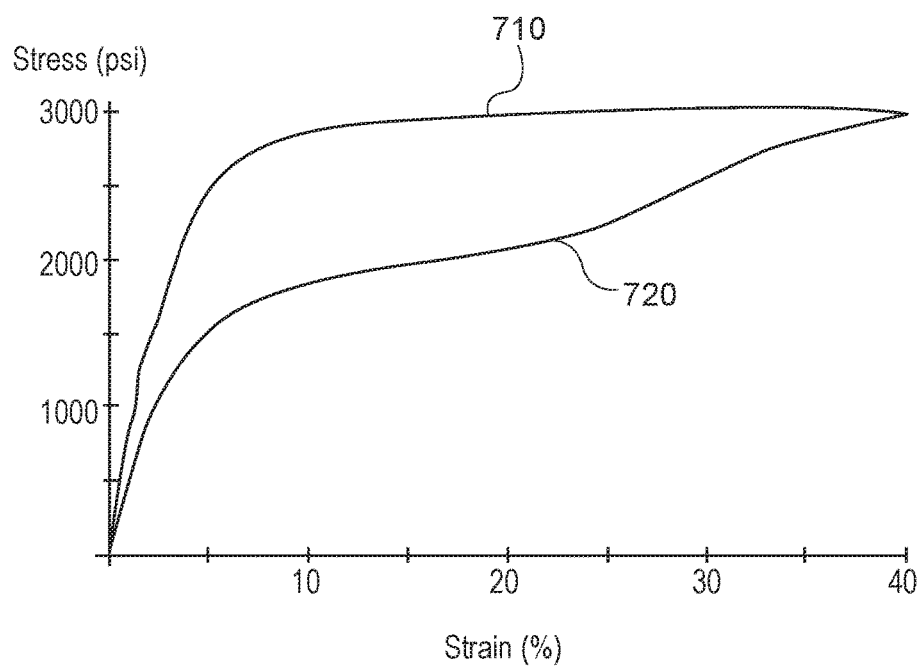
FIG. 12 is a graph of the resistive force versus the percent elongation comparing the behavior of the SELF web/backing layer as shown in FIG. 11 with an otherwise identical non-SELF'd web/backing layer.

In FIG. 12 there is shown a graph of the resistive force-elongation/strain curve of a SELF backing layer or web vs. a base backing layer or web, i.e., not including first and second regions. Specifically, Example No. 15 from Table 1 was used to generate curves 710 (base backing layer) and 720 (SELF backing layer). The method for generating the resistive force-elongation/strain curves is ASTM standard test method D 882—Tensile Testing of Thin Plastic Sheeting. The tensile test is performed at room temperature (about 22° C.) using a 2 inch gauge gap for the tesile tester. The sample to be tested is cut into a substantially rectilinear shape, for example, approximately 15 mm wide by approximately 75 mm long. A suitable instrument for this test includes a tensile tester from MTS Systems Corp., Eden Prairie, Minn., for example, Model Synergie 400. The instrument is interfaced with a computer. TestWorks 4™ software controls the testing parameters, performs data acquisition and calculations, and provides graphs and data reports. The comparison of a SELF backing layer vs. a base backing layer is shown below in Table 2:

TABLE 2

| Example #15 from Table 1 | Young's Modulus* (MPa) | Strain @ Yield (%) |
|---|---|---|
| Base Backing Layer (curve 710) | 478 | 28 |
| SELF Backing Layer (curve 720) | 254 | 81 |

*Machine Direction

The backing layer (Example #15 from Table 1) is SELF'd according to a process in which the toothed roll (the top roll) had teeth having a pitch of 0.060 inches, a tooth height of 0.075 inches, and a tooth spacing of 0.060 inches. The corners of the teeth were further rounded. The mating roll (bottom roll) was an un-toothed roll, that is, a roll having circumferentially extending ridges and grooves, similar to that shown in FIG. 19 above, and engaged at a depth of engagement (DOE) of about 0.045 inches. The SELF'ing process was carried out a room temperature at a rate of about 20 ft./min.

This demonstrates that the SELF backing layer or web exhibits a lower Young's Modulus/higher Strain@Yield vs. the base backing layer or web, resulting in a backing layer that is easier to stretch while maintaining uniform deformation.

Additional comparisons of SELF'd backing layers vs. base backing layers according to the present disclosure are shown in Table 3:

TABLE 3

Examples of SELF'd Backing Layers vs. Base Backing Layers

| Example No. | Example No. From Table 1 | Selfing activation | Depth of Engagement (inch) | Young's Modulus (MPa) | | Strain @ Yield (%) | | Strain @ Break (%) | |
|---|---|---|---|---|---|---|---|---|---|
| | | | | Base Film | SELF'd Film | Base Film | SELF'd Film | Base Film | SELF'd Film |
| 1 | #2 | cd tooling, then rotating | 0.045" | 458 | 219 | 31 | 66 | 495 | 170 |
| 2 | #2 | cd tooling, then rotating | 0.055" | 458 | 232 | 31 | 87 | 495 | 102 |

TABLE 3-continued

Examples of SELF'd Backing Layers vs. Base Backing Layers

| Example No. | From Table 1 | Selfing activation | Depth of Engagement (inch) | Young's Modulus (MPa) Base Film | Young's Modulus (MPa) SELF'd Film | Strain @ Yield (%) Base Film | Strain @ Yield (%) SELF'd Film | Strain @ Break (%) Base Film | Strain @ Break (%) SELF'd Film |
|---|---|---|---|---|---|---|---|---|---|
| 3 | # 5 | cd tooling, then rotating | 0.045" | 478 | 191 | 36 | 59 | 397 | 241 |
| 4 | # 5 | cd tooling, then rotating | 0.055" | 478 | 188 | 36 | 100 | 397 | 133 |
| 5 | # 8 | cd tooling, then rotating | 0.055" | 485 | 172 | 37 | 95 | 362 | 217 |
| 6 | # 3 | cd tooling, then rotating | 0.045" | 345 | 264 | 98 | 139 | 587 | 147 |
| 7 | # 3 | cd tooling, then rotating | 0.055" | 345 | 261 | 98 | 95 | 587 | 98 |
| 8 | # 9 | cd tooling, then rotating | 0.055" | 365 | 201 | 97 | 134 | 381 | 139 |
| 9 | # 11 | cd tooling, then rotating | 0.055" | 404 | 139 | 41 | 228 | 377 | 250 |
| 10 | # 13 | cd tooling, then rotating | 0.055" | 415 | 146 | 45 | 262 | 280 | 265 |
| 11 | # 15 | cd tooling, then rotating | 0.045" | 488 | 302 | 28 | 88 | 478 | 178 |
| 12 | # 15 | md tooling | 0.045" | 488 | 230 | 28 | 78 | 478 | 290 |

For Example Nos. 1 to 11 in Table 3, the backing layers are cut layer in machine direction, rotated 90° and then SELF'd with according to a process in which the toothed roll (the top roll) had teeth having a pitch of 0.060 inches, a tooth height of 0.075 inches, and a tooth spacing of 0.060 inches. The corners of the teeth were further rounded. The mating roll (bottom roll) was an un-toothed roll, that is, a roll having circumferentially to extending ridges and grooves, similar to that shown in FIG. 17 above, and engaged at a depth of engagement (DOE) listed in Table 3. The SELF'ing process was carried out a room temperature and hand cranked.

For Example No. 12 in Table 3, the backing layers are cut layer in machine direction, rotated 90° and then SELF'd with according to a process in which the toothed roll (the top roll) had teeth having a pitch of 0.060 inches, a tooth height of 0.075 inches, and a tooth spacing of 0.060 inches. The corners of the teeth were further rounded. The mating roll (bottom roll) was an un-toothed roll, that is, a roll having circumferentially extending ridges and grooves, similar to that shown in FIG. 19 above, and engaged at a depth of engagement (DOE) of about 0.045 inches. The SELF'ing process was carried out a room temperature at a rate of about 20 ft./min.

As can be seen from Table 3, the depth and frequency of rib-like elements can also be varied to control the available stretch of the SELF web. The available stretch is increased if for a given frequency of rib-like elements, the height or degree of deformation imparted on the rib-like elements is increased. Similarly, the available stretch is increased if for a given height or degree of deformation, the frequency of rib-like elements is increased.

Figure 13:
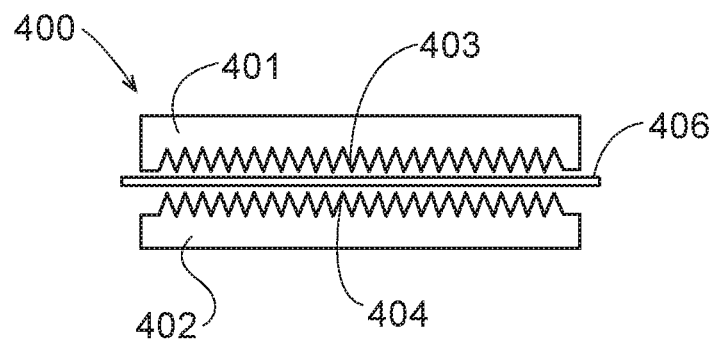
FIG. 13 is a simplified side elevational view of an exemplary apparatus used to form the SELF web/backing layer according to one or more embodiments illustrated and described herein.

Referring now to FIG. 13, there is shown one example of an apparatus 400 used to form the SELF web 52 shown in FIG. 11. Apparatus 400 includes plates 401, 402. Plates 401, 402 include a plurality of intermeshing teeth 403, 404, respectively. Plates 401, 402 are brought together under pressure to form the base film 406.

Figure 14:
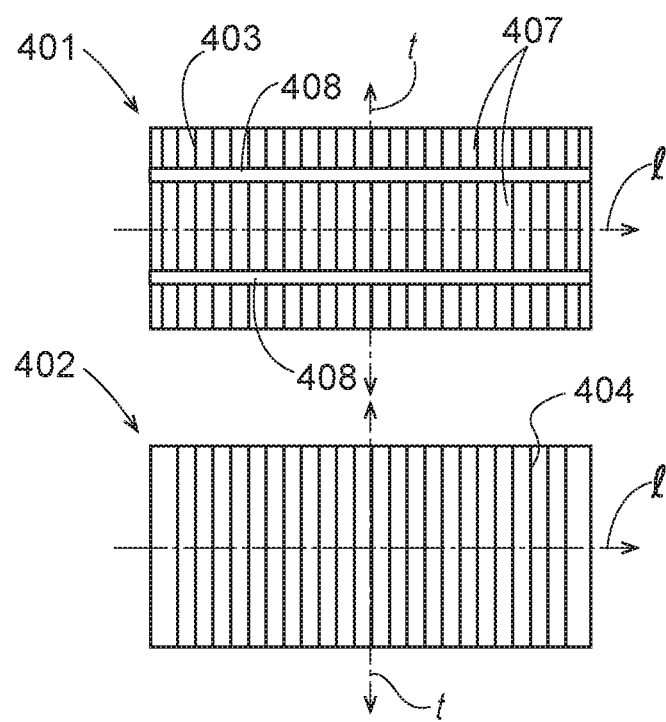
FIG. 14 is a plan view of the opposed meshing plates of the exemplary apparatus of FIG. 13 laid side-by-side with their meshing surfaces exposed.

Referring now to FIG. 14, it can be seen that plates 401 and 402 each have a longitudinal axis "l" and a transverse axis "t" which is substantially perpendicular to the longitudinal axis. Plate 401 includes toothed regions 407 and grooved regions 408 both which extend substantially parallel to the longitudinal axis of the plate 401. Within toothed regions 407 of plate 401 there are a plurality of teeth 403. Plate 402 includes teeth 404 which mesh with teeth 403 of plate 401. When the base film 406 is formed between plates 401, 402 the portions of the base film 406 which are positioned within grooved regions 408 of plate 401 and teeth 404 on plate 402 remain undeformed. These regions correspond with the first regions 204 of the SELF web 200 shown in FIG. 11. The portions of the base film 406 positioned between toothed regions 407 of plate 401 and teeth 404 of plate 402 are incrementally and plastically formed creating rib-like elements 214 in the second regions 206 of the SELF web 200.

Figure 15:
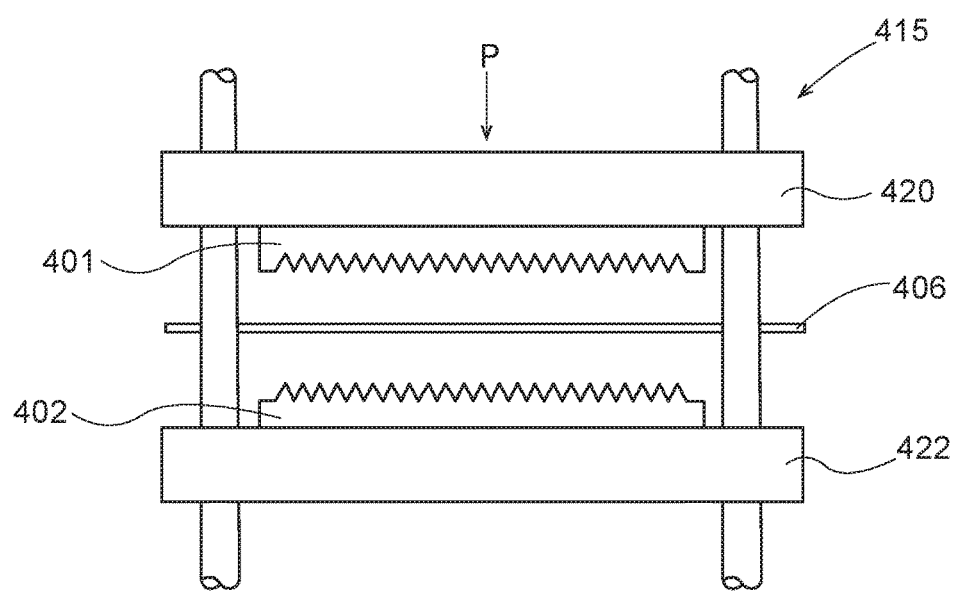
FIG. 15 is a simplified side elevational view of a static press used to form the SELF web/backing layer according to one or more embodiments illustrated and described herein.

In one embodiment, the method of formation can be accomplished in a static mode, where one discrete portion of a base film is deformed at a time. An example of such a method is shown in FIG. 15. A static press indicated generally as 415 includes an axially moveable plate or member 420 and a stationary plate 422. Plates 401 and 402 are attached to members 420 and 422, respectively. While plates 401 and 402 are separated, base film 406 is introduced between the plates, 401, 402. The plates are then brought together under a pressure indicated generally as "P". The upper plate 401 is then lifted axially away from plate 402 allowing the formed polymeric web to be removed from between plates 401 and 402.

Figure 16:
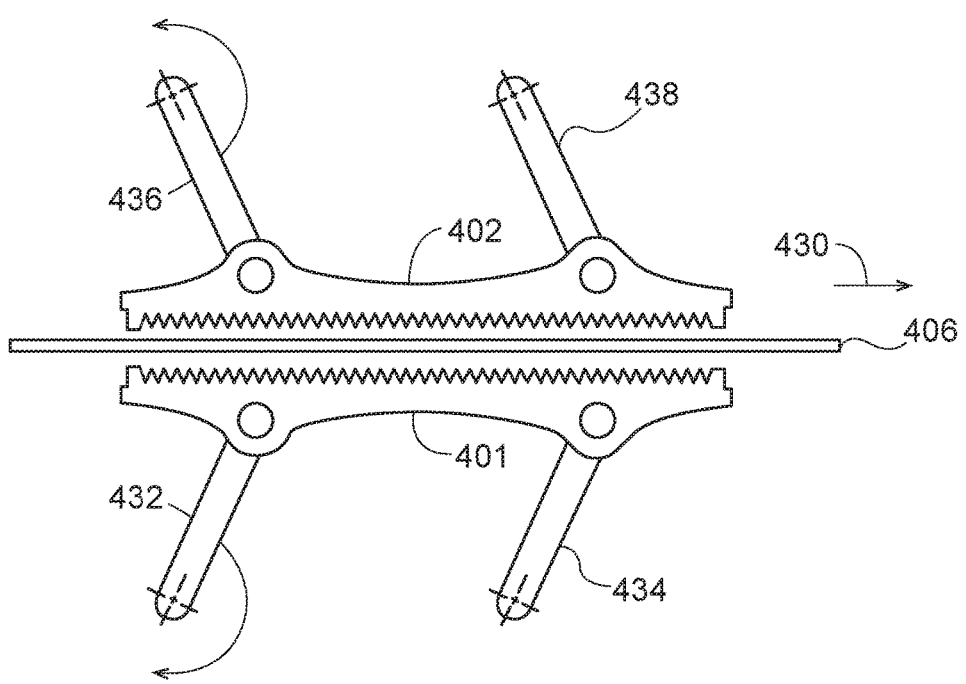
FIG. 16 is a simplified side elevational view of a continuous, dynamic press used to from the SELF web/backing layer according to one or more embodiments illustrated and described herein.

FIG. 16 is an example of a dynamic press for intermittently contacting the moving web and forming the base material 406 into a formed web similar to the SELF web 52 of FIG. 11. Polymeric film 406 is fed between plates 401 and 402 in a direction generally indicated by arrow 430. Plate 401 is secured to a pair of rotatably mounted arms 432, 434 which travel in a clockwise direction which move plate 401 in a similar clockwise motion. Plate 402 is connected to a pair of rotary arms 436, 438 which travel in a counter clockwise direction moving plate 402 in a counter clockwise direction. Thus, as web 406 moves between plates 401 and 402 in direction indicated by arrow 430, a portion of the base film between the plates is formed and then released such that the plates 401 and 402 may come back grab and deform another section of base film 406. This method has the benefit of allowing virtually any pattern of any complexity to be formed in a continuous process, for example, uni-directional, bi-directional, and multi-directional patterns.

The dynamic press of FIG. 16 could be used on a strip of material to form strainable networks into the completed product. For example, the entire or portions of the completed strip of material could be placed between plates 401 and 402 to create a strainable network in all layers of the strip of material.

Another method of forming the base material into a SELF web is vacuum forming. An example of a vacuum forming method is disclosed n commonly assigned U.S. Pat. No. 4,342,314, issued to Radel et al. on Aug. 3, 1982. Alternatively, the SELF web of the present disclosure may be hydraulically formed in accordance with the teachings of commonly assigned U.S. Pat. No. 4,609,518 issued to Curro et al. on Sep. 2, 1986. Each of the above said patents being incorporated herein by reference.

Figure 17:
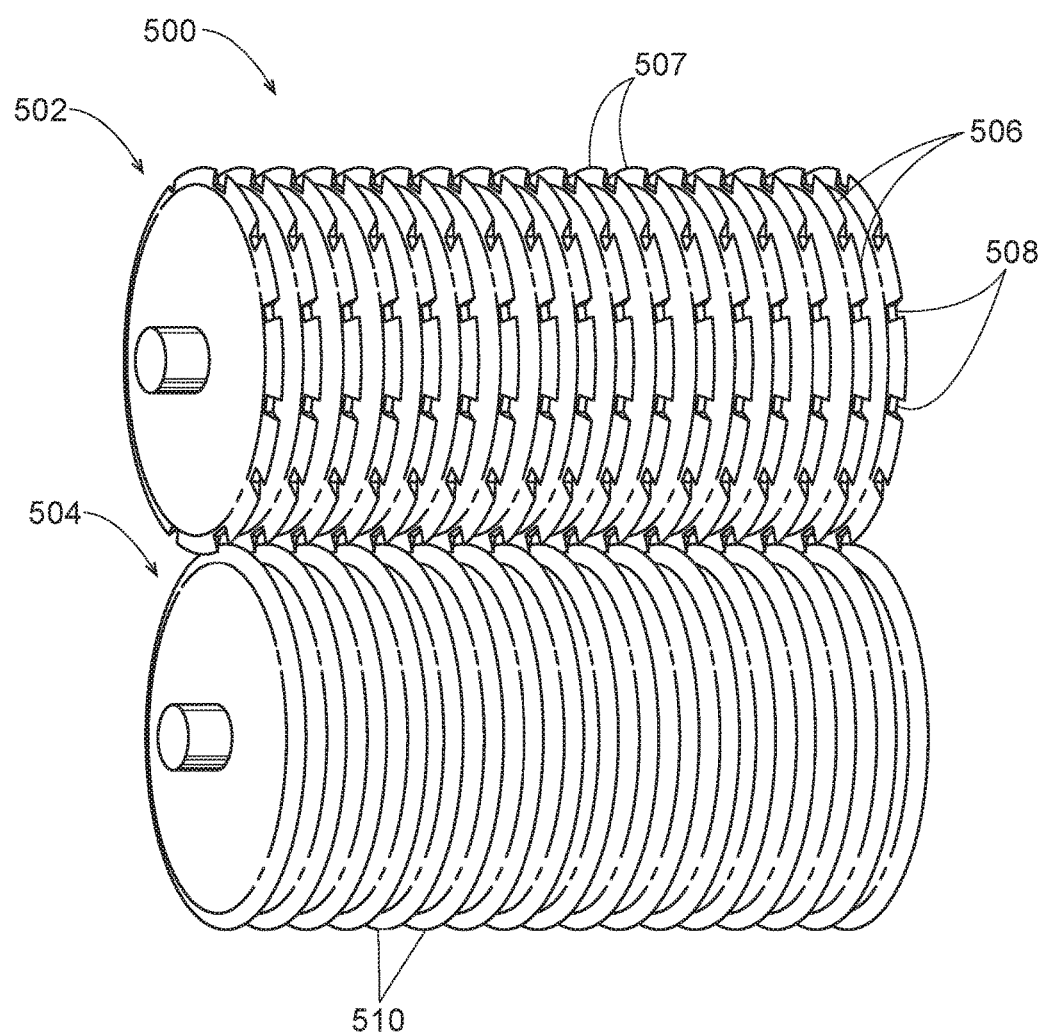
FIG. 17 is a simplified illustration of an exemplary apparatus used to form the SELF web/backing layer according to one or more embodiments illustrated and described herein.

In FIG. 17 there is shown another apparatus generally indicated as 500 for forming the base film into a formed SELF web, Apparatus 500 includes a pair of rolls 502, 504. Roll 502 includes a plurality of toothed regions 506 and a plurality of grooved regions 508 that extend substantially parallel to a longitudinal axis running through the center of the cylindrical roll 502, Toothed regions 506 include a plurality of teeth 507, Roll 504 includes a plurality of teeth 510 which mesh with teeth 507 on roll 502. As a base film is passed between intermeshing rolls 502 and 504, the grooved regions 508 will leave portions of the film undeformed producing the first regions of the SELF web 200 of FIG. 11. The portions of the film passing between toothed regions 506 and teeth 510 will be formed by teeth 507 and 510, respectively, producing rib-like elements in the second regions of the SELF web 200, The embodiment of FIG. 17 is referred to as CD or cross-machine direction SELFing, because the web 200 can be stretched in CD direction.

Alternatively, roll 504 may consist of a soft rubber. As the base film is passed between toothed roll 502 and rubber roll 504 the film is mechanically formed into the pattern provided by the toothed roll 502. The film within the grooved regions 508 will remain undeformed, while the film within the toothed regions 506 will be formed producing rib-like elements in the second regions.

Figure 18:
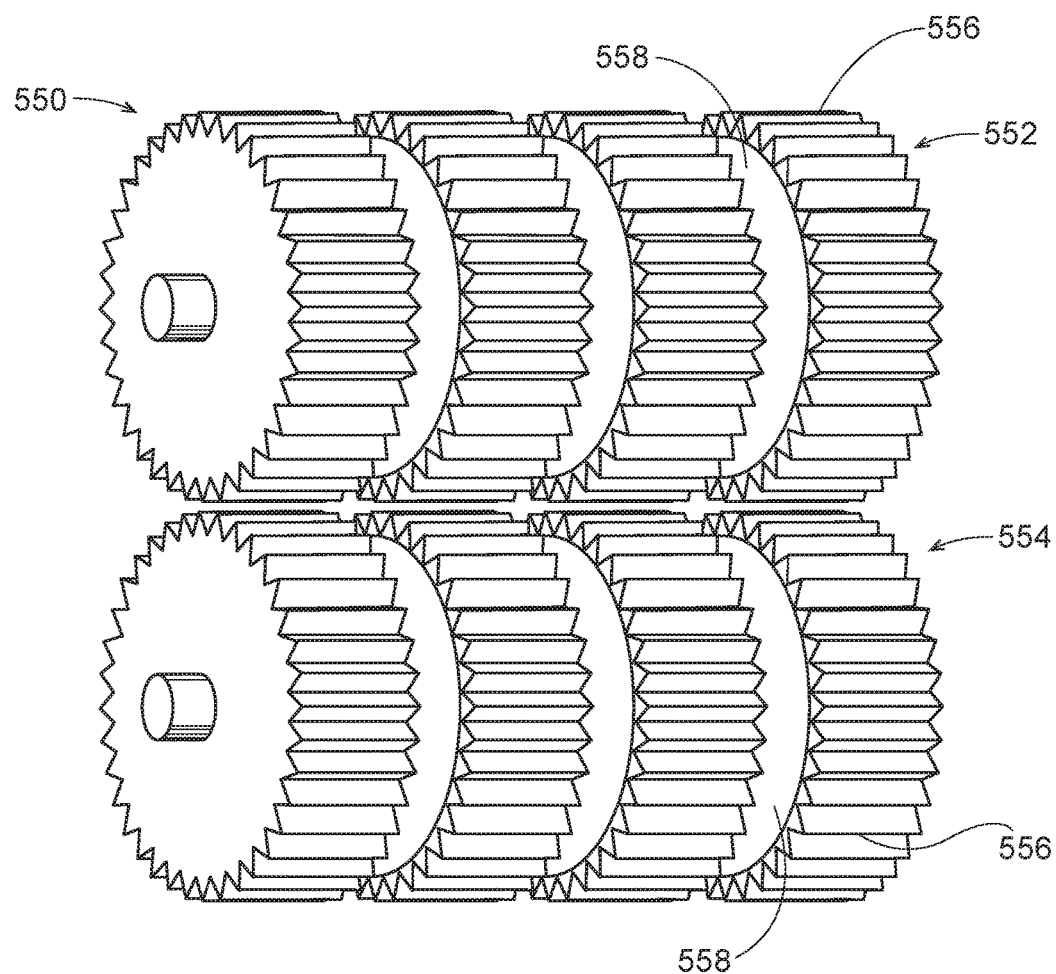
FIG. 18 is an illustration of another embodiment of an apparatus used to form the SELF web/backing layer according to one or more embodiments illustrated and described herein.

Referring now to FIG. 18, there is shown an alternative apparatus generally indicated as 550 for forming the base film into a SELF web in accordance with the teachings of the present disclosure, Apparatus 550 includes a pair of rolls 552, 554. Rolls 552 and 554 each have a plurality of toothed regions 556 and grooved regions 558 extending about the circumference of rolls 552, 554 respectively, As the base film passes between rolls 552 and 554, the grooved regions 558 will leave portions of the film undeformed, while the portions of the film passing between toothed regions 556 will he formed producing rib-like elements in second regions 206. The embodiment of FIG, 18 is referred to as MD or machine direction SELFing because the web 200 can be stretched in MD direction.

Figure 19:
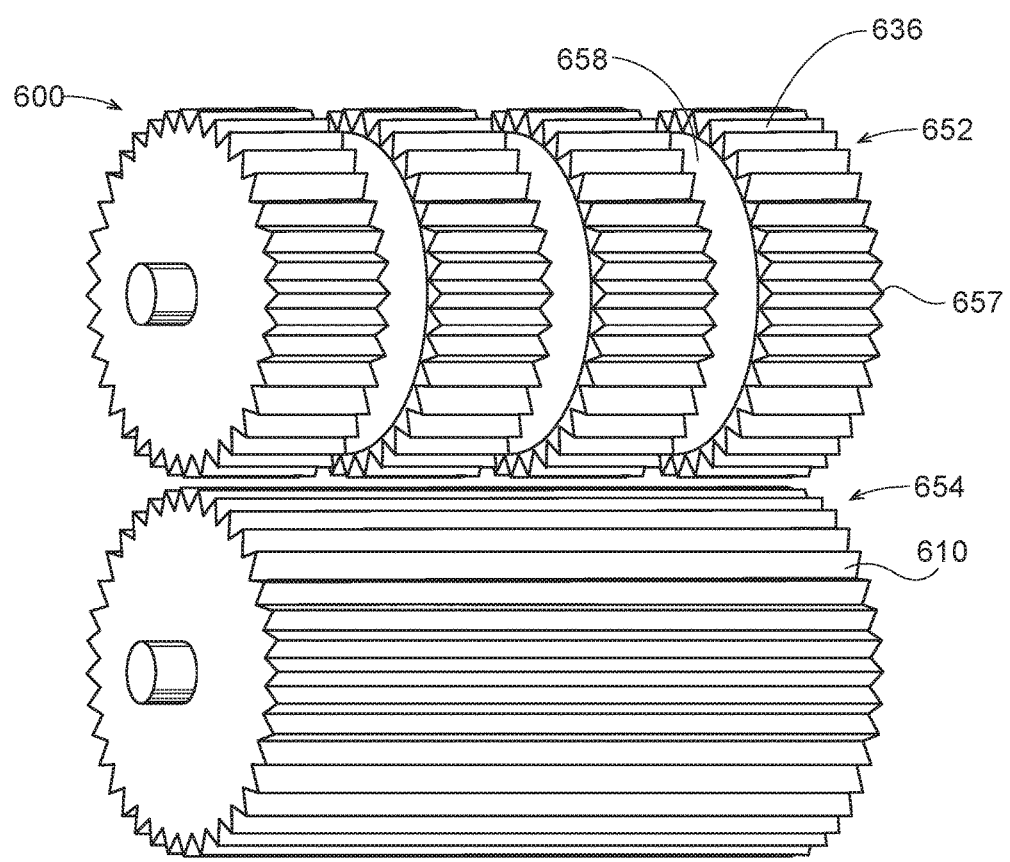
FIG. 19 is an illustration of yet another embodiment of an apparatus used to form the SELF web/backing layer according to one or more embodiments illustrated and described herein.

Referring now to FIG. 19, there is shown another embodiment indicated as 600 for forming the base film into a SELF web. Apparatus 600 includes a pair of rolls 652, 654. Roll 652 has a plurality of toothed regions 656 and grooved regions 658 extending about the circumference of roll 652. Roil 654 includes a plurality of teeth 610 which mesh with teeth 656 on roil 652. As the base film passes between rolls 652 and 654, the grooved regions 658 will leave portions of the film undeformed producing the first regions of the SELF web 200 of FIG. 11. The portions of the film passing between the toothed regions 656 and teeth 610 will be formed by teeth 657 and 610, respectively, producing rib-like elements in the second regions of the SELF web 200. The embodiment of FIG. 9 is also referred to as MD or machine direction SELFing because the web 200 can be stretched in MD direction.

The pair of rolls discussed above may include any number of teeth and grooves as desired. In addition, the teeth and grooves may be nonlinear, such as for example, curved, sinusoidal, zig-zag, etc. The size and amount of engagement of teeth and grooves may be of any desired dimensions. In one embodiment, the pitch of the teeth are from about 0.020 inches to about 0.180 inches; in another embodiment from about 0.030 inches to about 0.120 inches; in another embodiment from about 0.040 inches to about 0.100 to inches; and in yet another embodiment from about 0.050 inches to about 0.070 inches, or any individual value these ranges.

Figure 22:
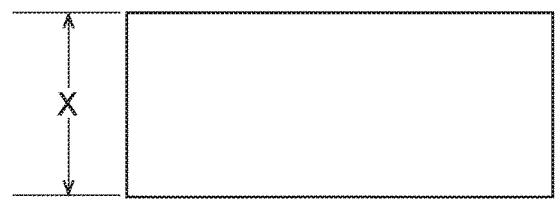
FIG. 22 is a plan view of one embodiment of a strip material before tensioning.
Figure 23:
FIG. 23 is a plan view of one embodiment of a tensioned strip of material.
Figure 24:
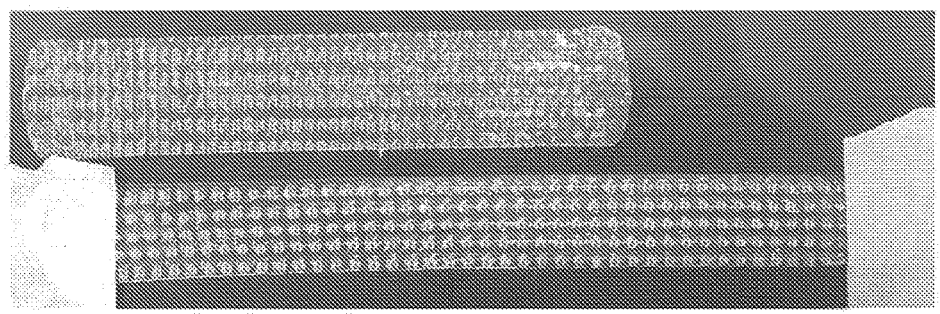
FIG. 24 is an image of a strip of material before and after tensioning.

With reference to FIGS. 22, 23, and 24 strip of material 810 may be stretchable in one embodiment to 100% elongation in multiple directions, (i.e. both parallel and perpendicular to a first direction), a width of neckable material shown schematically and having a width "X" such as, for example, about 15 mm, is tensioned so that it necks down to a width "Y" of about, for example, about 10 mm.

Figures 25A, 25B, 25C, 25D:
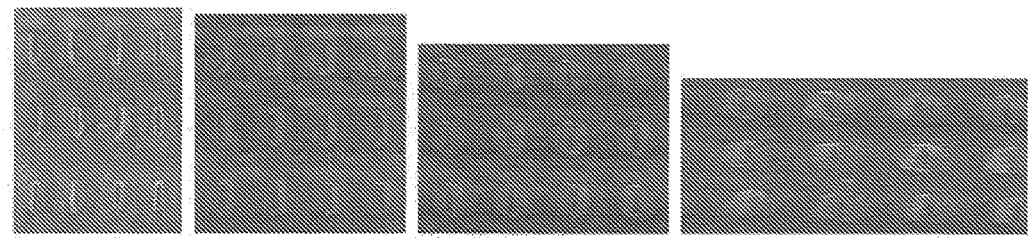
FIGS. 25A-D is an image of as strip of material at various stages of elongation.

As illustrated in FIGS. 25 A-D, the SELF'd strip of material according to the present disclosure can be stretched in one embodiment to 0%, 25%, 50% and 100% elongation. As can be seen, the strip of material maintains a uniform cross-sectional width or uniform extension as it is stretched from 0 to 100%. The elongation properties of a strip of material, specifically, Example No. 12 from Table 3 above, and the rib-like elements, are illustrated in Tables 4 and 5 below, respectively:

TABLE 4

| | Extensible strip | | | | | | |
|---|---|---|---|---|---|---|---|
| | Dimension (mm) | Area (mm$^2$) | % area change | Length (mm) | % length change | Width (mm) | % width change |
| Non-stretched | 15 × 76 | 1140 | | 76 | | 15 | |
| 25% stretched | 13.5 × 95 | 1282.5 | 12.50% | 95 | 25% | 13.5 | −10.00% |
| 50% stretched | 12 × 114 | 1368 | 20.00% | 114 | 50% | 12 | −20.00% |
| 100% stretched | 10 × 152 | 1520 | 33.33% | 152 | 100% | 10 | −33.33% |

TABLE 5

Extensible Strip

| | Width of rib-like elements (mm) | Height of rib-like elements (mm) | Distance btw. rib-like elements - center to center (mm) |
|---|---|---|---|
| Non-stretched | 0.36 | 1.31 | 1.63 |
| 25% stretched | 0.85 | 1.29 | 1.45 |
| 50% stretched | 1.26 | 1.22 | 1.27 |
| 100% stretched | 1.89 | 1.02 | 0.96 |

For Tables 4 and 5, the measurements were made under an optical microscope.

Backing layer or web material may be comprised of polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE® available from Dow Chemical Company and EXXACT® available from Exxon), and breathable polymers. The web materials may also be comprised of a synthetic woven, synthetic knit, nonwoven, apertured film, macroscopically expanded three-dimensional formed film, absorbent or fibrous absorbent material, foam filled composition or laminates and/or combinations thereof. The nonwovens may be made but not limited to any of the following methods: spunlace, spunbond, meltblown, carded and/or air-through or calender bonded, with a spunlace material with loosely bonded fibers being the preferred embodiment.

While the SELF web has been described as a single base layer of substantially planar polymeric film, other base materials or laminates of materials may also be used. Examples of base materials from which the SELF web can be made include two-dimensional apertured films and macroscopically expanded, three-dimensional, apertured formed films. Examples of macroscopically expanded, three-dimensional, apertured formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982 U.S. Pat. No. 4,463,045 issued to Ahr, et al. on Jul. 31, 1984; and U.S. Pat. No. 5,006,394 issued to Baird on Apr. 9, 1991. Each of these patents are incorporated herein by reference. Examples of other suitable base materials include composite structures or laminates of polymer films, nonwovens, and polymer films and nonwovens. Additional reinforcing elements can also be added for strength and recovery benefits.

In another embodiment, the backing layer 812 may be an elastomeric nonwoven substrate or an elastomeric film that does not require selfing. Non-limiting examples of suitable elastomeric materials include thermoplastic elastomers chosen from at least one of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Example styrenic block copolymers include styrene-butadiene-styrene, styrene-isoprene-styrene, styrene-ethyl-ene/butylenes-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Polymers, LP of Houston, Tex. Commercially available metallocene-catalyzed polyolefins include EXXPOL® and EXACT® from Exxon Chemical Company of Baytown, Tex.; AFFINITY®; and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del. Other particularly suitable examples of elastomeric materials include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical cross-links, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518, 378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene to with a low level comonomer (e.g., ethylene or a higher α-olefin) incorporated into the backbone. Suitable elastomeric RCP materials are available under the names VISTAMAXX® (available from ExxonMobil, Houston, Tex.) and VERSIFY® (available from Dow Chemical, Midland, Mich.).

In another embodiment, the backing layer 812 may be formed by a process for selectively aperturing a nonwoven web. In one embodiment, the nonwoven web may be extensible, elastic, or nonelastic. The nonwoven web may be a spunbonded web, a meltblown web, or a bonded carded web. If the nonwoven web is a web of meltblown fibers, it may include meltblown microfibers. The nonwoven web may be made of fiber forming polymers such as, for example, polyolefins. U.S. Pat. No. 5,916,661, entitled "Selectively Apertured Nonwoven Web" issued to Benson et al. on Jun. 29, 1999, discloses a process for selectively aperturing a nonwoven web and is incorporated herein by reference.

In another embodiment, the strip of material may be formed by a substance encapsulation system. U.S. Pat. No. 6,716,498, entitled "Applications For Substance Encapsulating Laminate Web" issued to Curro et al. on Apr. 6, 2004, disclosed a suitable substance application system and is incorporated herein by reference.

Surprisingly, we have found that strips of material with a SELF'd backing layer can be more easily stretched without causing sudden necking. Rather, the strip of material according to the present disclosure is uniformly deformed when it is stretched. These beneficial properties can be quantified by measuring certain characteristics of a strip of material, including Young's Modulus, % Strain@Break and % Strain@Yield. Strips of material according to the present disclosure may have a Young's Modulus of less than 50 MPa, in another embodiment less than 40 MPa, in yet another embodiment less than 30 MPa, and in yet another embodiment from about 15 MPa to about 50 MPa. In another embodiment, strips of material according to the present disclosure may have a % Strain@Break of greater than about 250%, in another embodiment of from about 250% to about 500% and in another embodiment of from about 200% to about 400%. In another embodiment, strips of material according to the present disclosure may have a % Strain@Yield of greater than about 25%, in another embodiment of from about 20% to about 300%, in another embodiment of from about 25% to about 200%, and in another embodiment of from about 30% to about 100%.

Oral Care Composition

The oral care composition is a composition, compound, or mixture capable of influencing or effecting a desired change in appearance and/or structure of the surface it contacts. Examples of appearance and structural changes include, but are not necessarily limited to, whitening, stain bleaching, stain removal, plaque removal, and tartar removal. According to the present disclosure, the oral care composition may be adhesive or non-adhesive and includes one or more oral care actives. In one embodiment, the active is for the whitening of the tooth surfaces.

Adhesive Composition

The adhesive is a composition, compound, or mixture capable of influencing or effecting a desired change in appearance and/or structure of the surface it contacts. Examples of appearance and structural changes include, but are not necessarily limited to, whitening, stain bleaching, stain removal, plaque removal, and tartar removal. According to the present disclosure, the adhesive composition includes one or more oral care actives. In one embodiment, the active is for the whitening of the tooth surfaces.

The adhesive composition may be coated on the strip of material, be applied by the user to the backing layer, or be applied by the user to their teeth and then the backing layer is placed over the coated teeth. The amount of adhesive applied to the backing layer or teeth will depend upon the size and capacity of the piece of material, concentration of the active, and the desired benefit. Generally, less than about 1 gram of substance is required. In certain embodiments, from about 0.05 grams to about 0.5 grams or from about 0.1 gram to about 0.4 grams of the substance is used. The amount of substance per square cm of material may be less than about 0.2 grams/cm$^2$, from about 0.005 to about 0.1 grams/cm$^2$, or from about 0.01 grams/cm$^2$ to about 0.04 grams/cm$^2$.

The adhesive may be in the form of a viscous liquid, paste, gel, aqueous gel, solution, or other suitable form that can provide sufficient adhesion. The substance may have a viscosity of from about 200 to about 1,000,000 cps, from about 100,000 to about 800,000 cps and more preferably from about 400,000 to about 600,000 cps at low shear rates (less than one 1/seconds).

In one embodiment, the adhesive composition may be an aqueous gelling agent. These gelling agents are safe for oral use, do not readily dissolve in saliva, and do not react with or inactivate the oral care compounds incorporated into them. Generally, the gelling agent is a swellable polymer. Furthermore, the gel formed with these agents provide sufficient adhesive attachment of the backing layer to the targeted area of the mouth. The level of gelling agent to form the gel composition is from about 0.1% to about 15%, in another embodiment from about 1% to about 10%, in another embodiment from about 2% to about 8%, and in yet another embodiment from about 4% to about 6%, by weight of the oral care composition or substance.

Suitable gelling agents include carboxypolymethylene, carboxymethyl cellulose, carboxypropyl cellulose, polyoxamers, carrageenan, Veegum, carboxyvinyl polymers, and natural gums such as gum karaya, xanthan gum, Guar gum, gum arabic, gum tragacanth, and mixtures thereof. In one embodiment, carboxypolymethylene obtained from B. F. Goodrich Company under the tradename Carbopol® is used. For example, Carbopols include Carbopol 934, 940, 941, 956 and mixtures thereof. Carboxypolymethylene is a slightly acidic vinyl polymer with active carboxyl groups. The normal concentration of various carboxypolymethylene resins in water, according to the manufacturer, is below about 2%. However, it has been found that by preparing supersaturated carboxypolymethylene compositions having an absolute concentration in the ranges specified above, suitable high viscosity oral gel compositions may be prepared.

The concentrated carboxypolymethylene gels have a number of important characteristics in addition to high viscosity. Enough carboxypolymethylene is added to the oral gel compositions beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip material against the targeted oral cavity surface it is affixed to, particularly teeth. However, care should be taken to avoid too much carboxypolymethylene thereby making insertion or withdrawal of the strip material difficult.

If the adhesive composition is an aqueous gel, the water present in the gel compositions should be deionized and free of organic impurities. Water comprises from about 0.1% to 95%, in another embodiment from about 5% to about 90%, and in yet to another embodiment from about 10% to about 80%, by weight of the oral care substance. This amount of water includes the free water that is added plus that amount that is introduced with other materials.

A pH adjusting agent may also be added to optimize the storage stability of the gel and to make the substance safe for oral tissue. These pH adjusting agents, or buffers, can be any material which is suitable to adjust the pH of the adhesive composition. Suitable materials include sodium bicarbonate, sodium phosphate, sodium hydroxide, ammonium hydroxide, sodium stannate, triethanolamine, citric acid, hydrochloric acid, sodium citrate, and combinations thereof. The pH adjusting agents are added in sufficient amounts so as to adjust the pH of the gel composition to about 4.5 to about 11, in another embodiment from about 5.5 to about 8.5, and in another embodiment from about 6 to about 7. pH adjusting agents are generally present in an amount of from about 0.01% to about 15% and in another embodiment from about 0.05% to about 5%, by weight of the adhesive composition.

While the gel described above provides sufficient adhesiveness, additional gelling agents may also be included in the formula to help the active ingredients adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 30,000,000. Still another possible adhesive suitable for use in the instant composition is a combination of Gantrez and the semisynthetic, water-soluble polymer carboxymethyl cellulose.

An additional carrier material may also be added to the adhesive composition, Carrier materials can be humectants. Suitable humectants include glycerin, sorbitol, polyethylene glycol, propylene glycol, and other edible polyhydric alcohols. Humectants are generally present in an amount of from about 10% to about 95% and in another embodiment from about 50% to about 80%, by weight of the adhesive composition. In addition to the above materials of the gel, a number of other components can also be added to the adhesive composition. Additional components include, but are not limited to, flavoring agents, sweetening agents, xylitol, opacifiers, coloring agents, and chelants such as ethylenediaminetetraacetic acid. These additional ingredients can also be used in place of the compounds disclosed above.

Oral Care Actives

As mentioned above, the oral care composition may include an oral care active at a level where upon directed use, promotes the benefit sought by the wearer without detriment to the oral surface it is applied to. Suitable for oral care actives include any material that is generally considered as safe for use in the oral cavity that provides changes to the overall health of the oral cavity, and specifically the condition of the oral surfaces the adhesive composition contacts. The level of oral care active is from about 0.01% to about 40%, in another embodiment from about 0.1% to about 30%, in another embodiment from about 0.5% to about 20%, and in yet another embodiment from about 1% to about 15%, by weight of the adhesive composition.

The following is a non all-inclusive list of oral care actives that may be used according to the present disclosure.

1. Teeth Whitening Actives

Teeth whitening actives may be included in the oral care substance. The actives suitable for whitening are selected from the group consisting of the peroxides, metal chlorites, perborates, percarbonates, peroxyacids, and combination thereof. Suitable peroxide compounds include hydrogen peroxide, calcium peroxide, carbamide peroxide, and mixtures thereof. Suitable metal chlorites include calcium chlorite, barium chlorite, magnesium chlorite, lithium chlorite, sodium chlorite, and potassium chlorite. Additional whitening actives may be hypochlorite and chlorine dioxide.

2. Phosphates

Anti-tartar agents known for use in dental care products includes phosphates. Phosphates include pyrophosphates, polyphosphates, polyphosphonates and mixtures thereof. Pyrophosphates are among the best known for use in dental care products. Pyrophosphate ions are delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are examples.

The pyrophosphate salts are described in more detail in Kirk & Othmer, Encyclopedia of Clinical Technology Third Edition, Volume 17, Wiley-Interscience. Publishers (1982), incorporated herein by reference in its entirety, including all references incorporated into Kirk & Othmer. Additional anticalculus agents include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg eon Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents to may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

3. Fluoride Ion Source

Fluoride on sources are well known for use in oral care compositions as anti-caries agents. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference, in one embodiment, the instant compositions provide from about 50 ppm to 10,000 ppm, and in another embodiment from about 100 to 3000 ppm, of fluoride ions in the aqueous solutions that contact dental surfaces when used with the strip of material used in the mouth.

4. Antimicrobial Agents

Antimicrobial agents can also be included in oral care substances according to the present disclosure. Such agents may include, but are not limited to, 5-chloro-2-(2,4-dichlorophenoxy)-phenol, commonly referred to as triclosan, and described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, substituted monoperthalic acid and its salts and esters as disclosed in U.S. Pat. No. 4,990,329, Feb. 5, 1991, U.S. Pat. No. 5,110,583, May 5, 1992 and U.S. Pat. No. 4,716,035, Dec. 29, 1987, all to Sampathkumar; preferably magnesium monoperoxy phthalate, chlorhexidine (Merck Index, no. 2090), alexidine (Merck Index, no. 222; hexetidine (Merck Index, no. 4624); sanguinarine (Merck index, no. 8320); benzalkonium chloride (Merck Index, no. 1066); salicylanilide (Merck index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

5. Anti-Inflammatory Agents

Anti-inflammatory agents can also be present in the oral care substances. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997, herein incorporated by reference. Disclosed therein are methods of preventing and, or treating primary and reoccurring squamous cell carcinoma of the oral cavity or oropharynx by topical administration to the oral cavity or oropharynx an effective amount of an NSAID.

6. Nutrients

Nutrients may improve the condition of the oral cavity and can be included in the oral care substances. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., 1997, pp 10-17; incorporated herein by reference.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf to drug information service), Wolters Kluer Company, St. Louis, Mo., 1997, pp. 3-10; incorporated herein by reference.

Oral nutritional supplements include amino acids, lipotropics, fish oil, and mixtures thereof, as disclosed in Drug Facts and Comparisons (loose leaf drug information service), Wolters Kluer Company, St. Louis, Mo., 1997, pp. 54-54e; incorporated herein by reference. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, corn oil, safflower oil, medium chain triglycerides as disclosed in Drug Facts and Comparisons (loose leaf drug information service), Wolters Kluer Company, St. Louis, Mo., 1997, pp. 55-57; incorporated herein by reference.

7. Enzymes

An individual or combination of several compatible enzymes can be included in the oral care substances. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. Proteases break down salivary proteins which are absorbed onto the tooth surface and form the pellicle; the first layer of resulting plaque. Proteases along with lipases destroy bacteria by lysing proteins and lipids which form the structural component of bacterial cell walls and membranes. Dextranases break down the organic skeletal structure produced by bacteria that forms a matrix for bacterial adhesion. Proteases and amylases, not only present plaque formation, but also prevent the development of calculus by breaking-up the carbohydrate-protein complex that binds calcium, preventing mineralization.

Enzymes useful in the present disclosure include any of the commercially available proteases, glucanohydrolases, endoglycosidases, amylases, mutanases, lipases to and mucinases or compatible mixtures thereof. Preferred are the proteases, dextranases, endoglycosidases and mutanases, most preferred being papain, endoglycosidase or a mixture of dextranase and mutanase. Additional enzymes suitable for use in the present invention are disclosed in U.S. Pat. No. 5,000,939 to bring et al., Mar. 19, 1991; U.S. Pat. No. 4,992,420 to Neeser, Feb. 12, 1991; U.S. Pat. No. 4,355,022 to Rabussay, Oct. 19, 1982; U.S. Pat. No. 4,154,815 to Pader, May 15, 1979; U.S. Pat. No. 4,058,595 to Colodney, Nov. 15, 1977; U.S. Pat. No. 3,991,177 to Virda et al., Nov. 9, 1976 and U.S. Pat. No. 3,696,191 to Weeks, Oct. 3, 1972; all incorporated herein by reference.

8. Mouth and Throat Products

Other materials that can be used include commonly known mouth and throat products. Such products are disclosed in Drug Facts and Comparisons (loose leaf drug information service), Wolters bluer Company, St. Louis, Mo., 1997, pp. 520b-527; incorporated herein by reference. These products include, but, are not limited to anti-fungal, antibiotic and analgesic agents.

9. Antioxidants

Antioxidants are generally recognized as useful in oral care substances. Antioxidants are disclosed in texts such as Cadenas and Packer, The Handbook of Antioxidants©, 1996 by Marcel Dekker, Inc., incorporated herein by reference. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

10. H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine to responses have been defined as H-1 receptors (Ash, A. S. F. & H. O, Schild, Brit. J. Pharmacol Chemother., Vol. 27 (1966), p. 427, incorporated herein by reference). Histamine also stimulates the secretion of acid by the stomach (Loew, E. R. &. O. Chickering, Proc. Soc. Exp. Biol. Med., Vol. 48 (1941), p. 65, incorporated herein by reference), increases the heart rate (Trendelenburg, U., J. Pharmacol., Vol. 130 (1960), p. 450, incorporated herein by reference), and inhibits contractions in the rat uterus (Dews, P. B. & J. D. P. Graham, Brit. J. Pharmacol. Chemother., Vol. 1 (1946), p. 278, incorporated herein by reference); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine H-2-Receptors", Nature, Vol. 236 (Apr. 21, 1972), pp. 385-390 (Black), incorporated herein by reference, as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are to disclosed in U.S. Pat. Nos. 5,294,433 and 5,364,616 Singer et al., issued Mar. 15, 1994 and Nov. 15, 1994 respectively and assigned to Procter &. Gamble; both herein incorporated by reference, wherein the selective H-2 antagonist is selected from the group consisting of cimetidine, etintidine, ranitidine, ICIA-5165, tiotidine, ORE-17578, lupitidine, donetidine, famotidine, roxatidine, pifatidine, lamtidine, BL-6548 BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and FH-408.4. Particularly preferred is cimetidine (SKF-92334), N-cyano-N'-methyl-N''-(2-(((5-methyl-1H-imidazol-4-yl)methyl)thio)ethyl)guanidine:

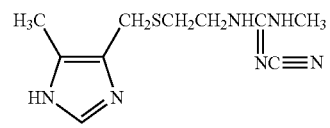

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

Release Liner

Figure 20:
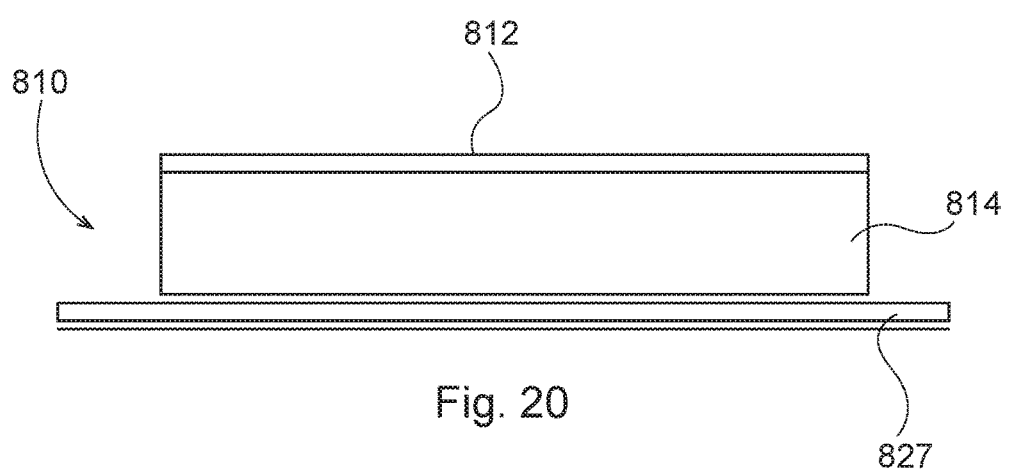
FIG. 20 is a perspective view of one embodiment of a strip of material including a backing layer, an oral care composition disposed thereon and a release liner according to one or more embodiments illustrated and described herein.

As mentioned above, the strip of material 810 may also include a release liner 827, as shown in FIG. 20. The release liner may be formed from any material which exhibits less affinity for substance than substance exhibits for itself and for the strip of material. The release liner may comprise a relatively rigid sheet of material such as polyethylene, paper, polyester, or other material which is then coated with a non-stick type material. The release liner material may be coated with wax, silicone, polyester such as Teflon®, fluoropolymers, or other non-stick type materials.

One suitable release liner is Scotchpak®, produced by 3M. The release liner may be cut to substantially the same size and shape as the backing layer or the release liner may be cut larger than the backing layer to provide a readily accessible means for separating the release liner from the backing layer. The release liner may be formed from a brittle material which cracks when the strip is flexed or from multiple pieces of material or a scored piece of material. Alternatively, the release liner may be in two overlapping pieces such as a typical adhesive strip bandage type design. A further description of materials suitable as release agents is found in Kirk-Othmer Encyclopedia of Chemical Technology, Fourth Edition, Volume 21, pp. 207-218, incorporated herein by reference.

Figure 21:
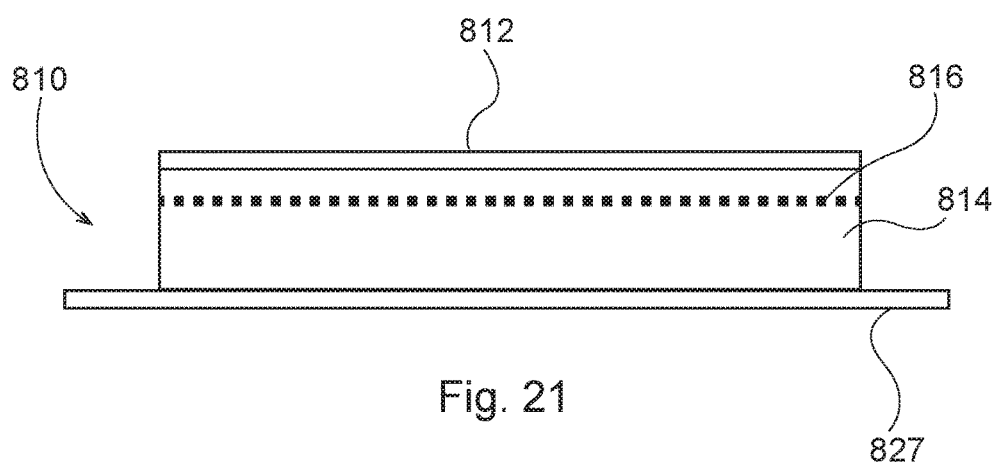
FIG. 21 is a perspective view of one embodiment of a strip of material including a backing layer, an oral care composition disposed thereon, a release liner, and a mesh liner according to one or more embodiments illustrated and described herein.

The strip of material 810 may also include a flexible, fractured plastic film or mesh 816 located between the release liner and the backing layer, as shown in FIG. 21. In one embodiment, the mesh layer is embedded within the oral care or adhesive composition. A suitable mesh layer is DELNET®, available from DelStar Technologies, Inc., Middletown, Del. The mesh liner may be cut to substantially the same size and shape as the backing layer. DELNET® is a mesh layer material made from high density polyethylene, low density polyethylene, linear low density polyethylene, polypropylene, polyvinyl acetate or blends of these polymers. DELNET® has an air porosity from 200 cfm to 2000 cfm, a thickness of from about 0.001 inches to about 0.010 inches, and a basis weight from 0.10 Oz/sy to 2.50 Oz/sy.

EXAMPLES

The following examples are given solely for the purposes of illustration and are not to be construed as limitations of the present disclosure.

Examples 1-12 shown in Table 6 below are embodiments of oral care compositions for use with a strip in accordance with the present disclosure.

TABLE 6

Example Oral Care Compositions

| | 1 | 2 | 3 | 4 | 5 | 6 |
|---|---|---|---|---|---|---|
| Glycerin | 10.000% | 10.000% | 20.000% | 10.000% | — | — |
| Water | 67.776% | 64.348% | 54.348% | 64.248% | 74.148% | 67.776% |
| Hydrogen Peroxide (35% Solution) | 15.143% | 18.571% | 18.571% | 18.571% | 18.571% | 15.143% |
| Carboxypolymethylene | 4.500% | 4.500% | 4.500% | 4.500% | 4.500% | 4.500% |
| Sodium Hydroxide (50% Solution) | 2.000% | 2.000% | 2.000% | 2.000% | 2.000% | 2.000% |
| Sodium Saccharin | — | — | — | 0.100% | 0.200% | — |
| Sodium Stannate | 0.200% | 0.200% | 0.200% | 0.200% | 0.200% | 0.200% |
| Sodium Pyrophosphate | 0.381% | 0.381% | 0.381% | 0.381% | 0.381% | 0.381% |
| Propylene Glycol | — | — | — | — | — | 10.000% |
| Pluronic 407 | — | — | — | — | — | — |

| | 7 | 8 | 9 | 10 | 11 | 12 |
|---|---|---|---|---|---|---|
| Glycerin | 10.000% | — | 3.000% | 15.000% | 10.000% | 10.000% |
| Water | 68.157% | 57.276% | 72.576% | 63.076% | 72.919% | 66.955% |
| Hydrogen Peroxide (35% Solution) | 15.143% | 15.143% | 17.143% | 15.143% | — | 17.143% |
| Carboxypolymethylene | 4.500% | — | 4.500% | 4.500% | 4.500% | 4.500% |
| Sodium Hydroxide (50% Solution) | 2.000% | 2.000% | 2.200% | 1.700% | 2.000% | — |
| Sodium Saccharin | — | — | — | — | — | — |
| Sodium Stannate | 0.200% | 0.200% | 0.200% | 0.200% | 0.200% | — |
| Sodium Pyrophosphate | — | 0.381% | 0.381% | 0.381% | 0.381% | — |
| Propylene Glycol | — | — | — | — | — | — |
| Pluronic 407 | — | 25.000% | — | — | — | — |
| Potassium Hydroxide | — | — | — | — | — | 1.403% |
| Carbamide Peroxide | — | — | — | — | 10.000% | — |

For Table 6 above, the values of peroxide active percentages and concentrations are measured using the following method. The package containing the peroxide system is stored for the stated period of time (e.g., 12 months) and conditions. After the stated storage time period, the peroxide concentration is measured using the Iodometric titration method. The Iodometric titration method is a standard method known in the art for measuring peroxide concentration. In general, the method is performed by weighing the substrate and composition containing the peroxide active, dissolving the composition in 1M sulfuric acid, and reacting the peroxide with an excess of potassium iodide in the presence of ammonium molybdate. This is then titrated with a known concentration of sodium thiosulfate to a clear endpoint using a starch indicator. The substrate is weighed upon completion of the titration and the composition weight is determined by difference. The peroxide concentration in the composition is then calculated. When the storage period is long, the concentration of the peroxide active can alternatively be determined by measuring the concentration as described above after at least one hundred and twenty days and then extrapolating for the remainder of the period using first order kinetics, as is known in the art. The above-described method is performed just after manufacture of a peroxide product and at the end of the specified storage period in order to determine the absolute peroxide concentrations as well as the percentage of the original concentration remaining, as is known in the art.

Examples 13-15 shown below are embodiments of oral care compositions for use with a strip in accordance with the present disclosure.

The following abbreviations and tradenames are used in the following examples:

Eudragit L 100-55 methacrylic acid copolymer, (Rohm America Inc.)
PEG polyethylene glycol 400
PVP30 Plasdone® K30 polyvinylpyrrolidone (ISP)
PVP90 Kollidon® 90F polyvinylpyrrolidone (BASF)

Example 13

Preparation of a Solid Composition

The following composition for tooth whitening was prepared from the following ingredients using a melt extrusion process:

| *Eudragit L 100-55 | 9 wt % |
|---|---|
| PVP90 | 44 wt % |
| PEG | 22 wt % |
| Hydrogen peroxide | 6 wt % |
| Water, stabilizers, pH modulators | 19 wt % |

The ingredients were melt processed in a Brabender single screw extruder as follows: The Eudragit L 100-55 was added to the extruder first, followed by PVP90 and PEG, at a temperature of 100 to 150° C. The composition was extruded to a thickness of 0.35 mm between two polyethylene terephthalate release liners. Hydrogen peroxide solution was added to the extruded film.

Example 14

Preparation of a Non-Solid Composition

A composition for tooth whitening was prepared from the following ingredients (Formula A):

| Deionized water | 35.0 wt % |
|---|---|
| Ethanol | 35.0 wt % |

-continued

| | |
|---|---|
| Eudragit L 100-55 | 4.00 wt % |
| PEG | 1.00 wt % |
| PVP90 | 7.00 wt % |
| Carbamide peroxide | 18.0 wt % |
| Sodium citrate | 0.13 wt % |

The composition was mixed in a Cole-Parmer high-torque low-speed lab mixer supplied with Teflon coated impeller (2 inches in diameter) as follows. Deionized water was mixed with ethanol, followed by the addition of PEG. Sodium citrate was then added under vigorous stirring conditions. Eudragit L 100-55 powder was added slowly (within 2-5 min) under vigorous stirring (500-600 rpm). After about 5-10 min (it is not necessary to wait until all Eudragit is dissolved), PVP90 powder was slowly added (within 5 min) The high stirring rate was maintained over 5-10 min. Carbamide peroxide powder was added (within 1-2 min) and the mixture stirred to obtain a homogeneous solution (approximately 30 minutes at 800-900 rpm). The solution was then stored over a period of 2-5 hours to let the air bubbles dissipate.

Example 15

Preparation of a Non-Solid Composition

A composition for tooth whitening was prepared from the following ingredients (Formula B):

| | |
|---|---|
| Deionized water | 35.0 wt % |
| Ethanol | 35.0 wt % |
| Eudragit L 100-55 | 2.50 wt % |
| PEG | 1.92 wt % |
| PVP90 | 6.00 wt % |
| Carbamide peroxide | 18.0 wt % |
| Sodium Citrate | 0.08 wt % |
| Methocel A4C | 1.50 wt % |

The composition was mixed in a Cole-Parmer high-torque low-speed lab mixer supplied with Teflon coated impeller (2 inches in diameter). Deionized water was mixed with ethanol, followed by the addition of PEG. Sodium citrate was then added under vigorous stirring conditions. Eudragit L 100-55 powder was added slowly (within 5 min) under vigorous stirring (500-600 rpm), followed by the slow (within 5 min) addition of Methocel A4C powder under vigorous stirring (500-600 rpm). After about 10 min, PVP90 powder was slowly added (within 5 min). The high stirring rate was maintained over 5-10 min. Carbamide peroxide powder was added (within 1-2 min) and the mixture stirred to obtain a homogeneous solution (approximately 30-60 minutes at 500-800 rpm). The solution was then stored over a period of 2-5 hours to let the air bubbles dissipate.

The following Examples (16-30) in Table 7 provide a comparison between teeth whitening strips that are commercially available to strips of material for the delivery of an oral care active according to the present disclosure.

TABLE 7

| Example | Thickness mm | Young's Modulus MPa | % Strain @Break % | % Strain @ Yield % |
|---|---|---|---|---|
| 16 | 0.20 | 19 | 346 | 60 |
| 17 | 0.20 | 21 | 302 | 267 |
| 18 | 0.20 | 45 | 324 | 35 |
| 19 | 0.20 | 62 | 45 | 31 |
| 20 | 0.20 | 29 | 193 | 141 |
| 21 | 0.08 | 294 | 21 | 8 |
| 22 | 0.19 | 44 | 64 | 39 |
| 23 | 0.13 | 440 | 24 | 8 |
| 24 | 0.20 | 25 | 388 | 22 |
| 25 | 0.20 | 22 | 944 | 16 |
| 26 | 0.18 | 68 | 31 | 27 |
| 27 | 0.41 | 68 | 97 | 83 |
| 28 | 0.94 | 81 | 60 | 25 |
| 29 | 0.87 | 95 | 59 | 24 |
| 30 | 0.24 | 46 | 396 | 7 |

Examples 16-18 are embodiments of strips of material for the delivery of an oral care active in accordance with the present disclosure. These Examples were made using Example No. 12 in Table 3 as the backing layer. Example 17 was aged in a roll stock for an additional 3 weeks more than Example 16. Example 18 also included a DELNET located between the release liner and the backing layer as shown in FIG. 21.

Example 19 is a commercially available whitening strip sold by The Procter and Gamble Company under the trademark CREST 3D WHITE WHITESTRIPS ADVANCED SEAL PROFESSIONAL EFFECT (Lot #1116BT3).

Example 20 is a commercially available whitening strip sold by The Procter and Gamble Company under the trademark CREST WHITESTRIPS 3D WHITE GENTLE ROUTINE (Lot #2206BT2).

Example 21 is a commercially available whitening strip sold by McNeil-PPC, Inc. under the trademark REMBRANDT STAIN DISSOLVING STRIPS (Lot #0192RD).

Example 22 is a commercially available whitening strip sold by LG Health and Beauty under the trademark CLAREN DENTAL WHITENING SOLUTION—NIGHT EFFECT (Lot #041027).

Example 23 is a commercially available whitening strip sold by Lornamead, Inc. under the trademark NATURAL WHITE dSolve (Lot #T4L039).

Example 24 is a commercially available whitening strip sold by Onuge Oral Care (Guangzhou) Limited under the trademark DENTAL WHITENING STRIPS.

Example 25 is a commercially available whitening strip sold by Xiamen YYX Trading Co., Ltd. under the trademark HEIDELBERG WHITESTRIPS (Lot #B 110909).

Example 26 is a commercially available whitening strip sold by Walgreen Co. under the trademark WALGREENS DENTAL STRIPS (Lot #058021).

Example 27 is a commercially available whitening strip sold by Target Brands, Inc. under the trademark UP & UP ADVANCED PLUS WHITENING STRIPS (Lot #012657 A1).

Example 28 is a commercially available whitening strip sold by Wal-Mart Stores Inc. under the trademark EQUATE DENTAL WHITENING STRIPS (Lot #021007B2).

Example 29 is a commercially available whitening strip sold by The Kroger Co. under the trademark KROGER WHITENING WRAPS (Lot #021621B1).

Example 30 is a commercially available whitening strip sold by CAO Group Inc. under the trademark SHEER WHITE (Lot #120207).

The method for generating the resistive force-elongation/strain data for Table 7 is ASTM standard test method D 882—Tensile Testing of Thin Plastic Sheeting, as described above, with the following modifications: Load Cell is 100 N; Gauge Length (grip separation) is 1.0 inch; Test Speed is 15.0 mm/sec; and Specimen Dimensions are 6.5 mm width× 25.4 mm length.

The following Examples in Tables 8 and 9 provide data for various teeth whitening strips measured according to the Strip Removal Test described in detail below.

TABLE 8

Strip Removal Results for Sample Teeth Whitening Products-Amount of Material Remaining After Peel Test

| | | Material left on glass rods (avg) | | | | Material collected (avg) |
|---|---|---|---|---|---|---|
| | | Gel | | Backing | | Gel + Backing |
| Examples | Test | length (mm) | % length | Length (mm) | % length | wt (g) |
| Example 19 from Table 7 | Initial Peel | 0 | 0 | 0 | 0 | 0 |
| | After 30 min in water | 0 | 0 | 0 | 0 | 0 |
| | After 1 hr in water | 0 | 0 | 0 | 0 | 0 |
| Example 17 from Table 7 | Initial Peel | 0 | 0 | 0 | 0 | 0 |
| | After 30 min in water | 0 | 0 | 0 | 0 | 0 |
| | After 1 hr in water | 0 | 0 | 0 | 0 | 0 |
| Example 30 from Table 7 | Initial Peel | 48 | 96 | 40 | 80 | 0.0905 |
| | After 30 min in water | 48 | 96 | 29 | 58 | 0.066 |
| | After 1 hr in water | 42 | 84 | 21 | 42 | 0.0418 |

% length is calculated by material weight/strip weight on glass rods/50 mm

TABLE 9

Strip Removal Results for Sample Teeth Whitening Products - Peel Force

| | Peel Force (N) (avg) | | |
|---|---|---|---|
| Examples | Initial Peel | After 30 min in water | After 1 hr in water |
| Example 19 from Table 7 | 0.2570 | 0.2391 | 0.1861 |
| Example 17 from Table 7 | 0.4509 | 0.3751 | 0.3547 |
| Example 30 from Table 7 | 1.9849 | 0.9825 | 0.9039 |
| Example 20 from Table 7 | 0.0052 | Not able to measure | Not able to measure |
| Example 24 from Table 7 | 0.0024 | Not able to measure | Not able to measure |
| Example 25 from Table 7 | 0.0077 | Not able to measure | Not able to measure |

Consumers generally prefer teeth whitening products to be easily and cleanly removed from their teeth. One way to compare ease of removal/clean removal for teeth whitening strips is to measure peel force and amount of material remaining after peel test. As shown in Tables 8 and 9, a Strip Removal Test was performed on representative teeth whitening products and the strip removal results were calculated.

In one embodiment, strips of material for deliver of an oral care active according to the present disclosure may have an initial peel force of greater than about 0.05 N. In another embodiment, strips of material for deliver of an oral care active may have an initial peel force of greater than about 0.10 N. In another embodiment, strips of material for deliver of an oral care active may have an initial peel force of greater than about 0.20 N. In yet another embodiment, strips of material for deliver of an oral care active may have an initial peel force of greater than about 0.30 N. In another embodiment, strips of material for deliver of an oral care active may have an initial peel force of greater than about 0.40 N. In another embodiment, strips of material for deliver of an oral care active may have an initial peel force of from about 0.05 N to about 1.0 N and in another embodiment from about 0.10 N to about 0.60N.

In one embodiment, strips of material for deliver of an oral care active according to the present disclosure may have less than about 0.05 g of material (gel+backing layer) remaining after an initial peel test. In another embodiment, strips of material for deliver of an oral care active may have less than about 0.025 g of material remaining after an initial peel test. In another embodiment, strips of material for deliver of an oral care active may have about 0.0 g of material remaining after an initial peel test. In another embodiment, strips of material for deliver of an oral care active may have from about 0.0 g to about 0.05 g of material remaining after an initial peel test.

Test Methods

The test methods and apparatus described below may be useful in testing embodiments of the present disclosure:

Two Cycle Hysteresis Test

This method is used to determine properties of strips of material, which may correlate with the forces experienced by the consumer during application and use. The two cycle hysteresis test is performed at room temperature (about 22° C.). The sample to be tested is cut into a substantially rectilinear shape, for example (approximately 0.20 mm thick, approximately 15 mm wide by approximately 76 mm long). A suitable instrument for this test includes a tensile tester from MTS Systems Corp., Eden Prairie, Minn., for example, Model Synergie 400. The instrument is interfaced with a computer. TestWorks 4™ software controls the testing parameters, performs data acquisition and calculations, and provides graphs and data reports.

The grips used for the test are wider than the sample. The grips are air actuated grips designed to concentrate the entire gripping force along a single line perpendicular to the direction of testing stress having one flat surface and an opposing face from which protrudes a half round (radius=6 mm) to minimize slippage of the sample.

The load cell is selected so that the forces measured will be between 10% and 90% of the capacity of the load cell or the load range used. A 100 Newton load cell may be used. The fixtures and grips are installed. The instrument is calibrated according to the manufacturer's instructions. The distance between the lines of gripping force (gauge length) is 2 inches (50.8 mm), which is measured with a steel ruler held beside the grips, unless specified otherwise. The load reading on the instrument is zeroed to account for the mass of the fixture and grips. The mass, thickness, and basis weight of the specimen are measured before testing. The specimen is mounted into the grips in a manner such that there is no slack and the load measured is between 0.00 Newton and 0.02 Newton, unless specified otherwise.

The two cycle hysteresis test method for strip samples involves the following steps (all strains are engineering strains):

(1) Strain the sample to 50% at a constant crosshead speed of 5 mm per second;
(2) Hold for 2 minutes;
(3) Reduce strain to 40% strain;
(4) Hold for 10 minutes.

Figure 26:
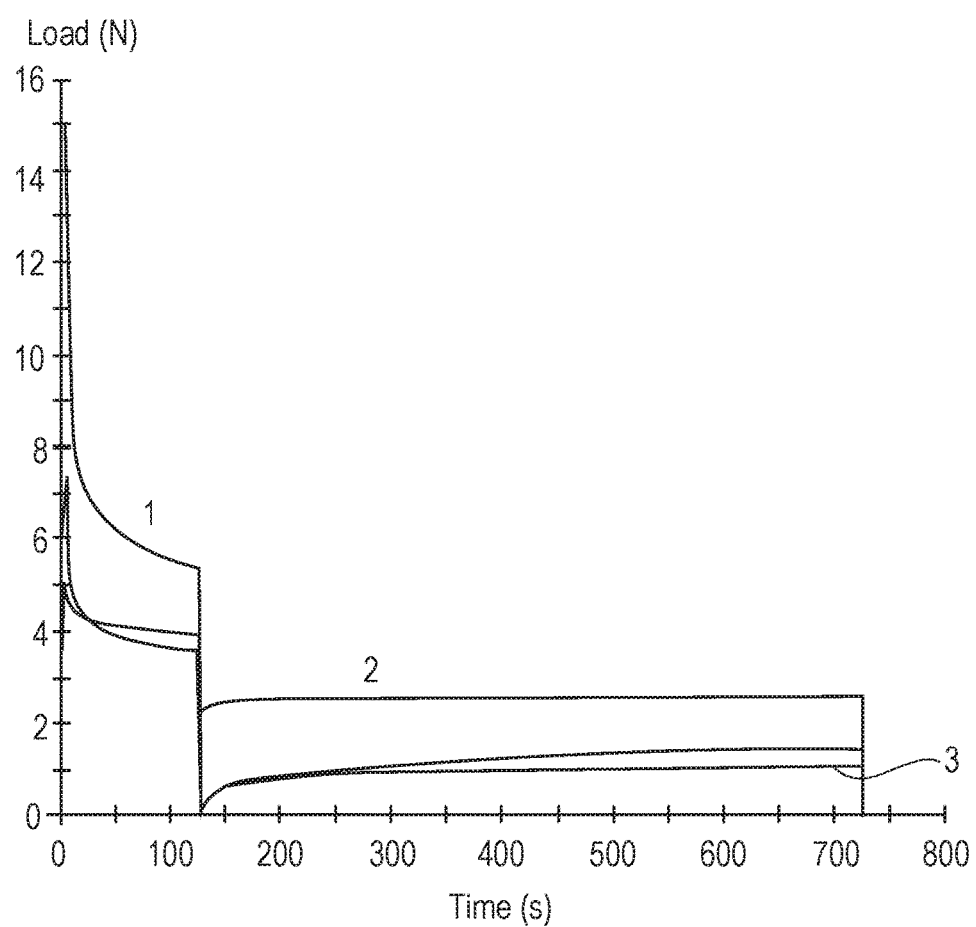
FIG. 26 illustrates the elastic hysteresis behavior of various test strips.

A graph of two cycles is generated. FIG. 26 sets forth the two cycle hysteresis data as measured by the above procedure for Samples 1, 2 and 3. Sample 1 is a current commercial product, Crest 3D White Whitestrips, Advanced Seal, Professional Effect™ (a product of the Procter & Gamble Company, Cincinnati, Ohio). Sample 2 is a strip of material having the same adhesive composition as Sample 1, but having a backing layer that is an elastic film (80% Affinity (PL 1850 from Dow)/20% LDPE (Petrothene NA 963 from Equistar). Further, the backing layer of Sample 2 has a 0.05 mm thickness. Sample 3 is a strip of material in accordance with the present disclosure and includes the same adhesive composition as Sample 1 and the backing layer of Example No. 15 from Table 1. Further, the backing layer of Sample 3 is SELF'd according to a process in which the toothed roll (the top roll) had teeth having a pitch of 0.060 inches, a tooth height of 0.075 inches, and a tooth spacing of 0.060 inches. The corners of the teeth were further rounded. The mating roll (bottom roll) was an un-toothed roll, that is, a roll having circumferentially extending ridges and grooves, similar to that shown in FIG. 19 above, and engaged at a depth of engagement (DOE) of about 0.045 inches. The SELF'ing process was carried out a room temperature at a rate of about 58 ft/min (18 m/min).

As can be seen from FIG. 26, the data demonstrates that Sample 1 has a high initial pulling force, Sample 2 has a high creeping recovery force and Sample 3 has both low initial pulling force and low creeping recovery force. Pulling force is related to how easy the strip is stretched. The lower pulling force, the easier the strip can be stretched. Creeping recovery force is related to the remaining force on the teeth after the strip is put on the teeth. The higher the creeping force, the more pulling tension may be applied on the teeth, leading to for example, headaches of the wearer.

Figure 27:
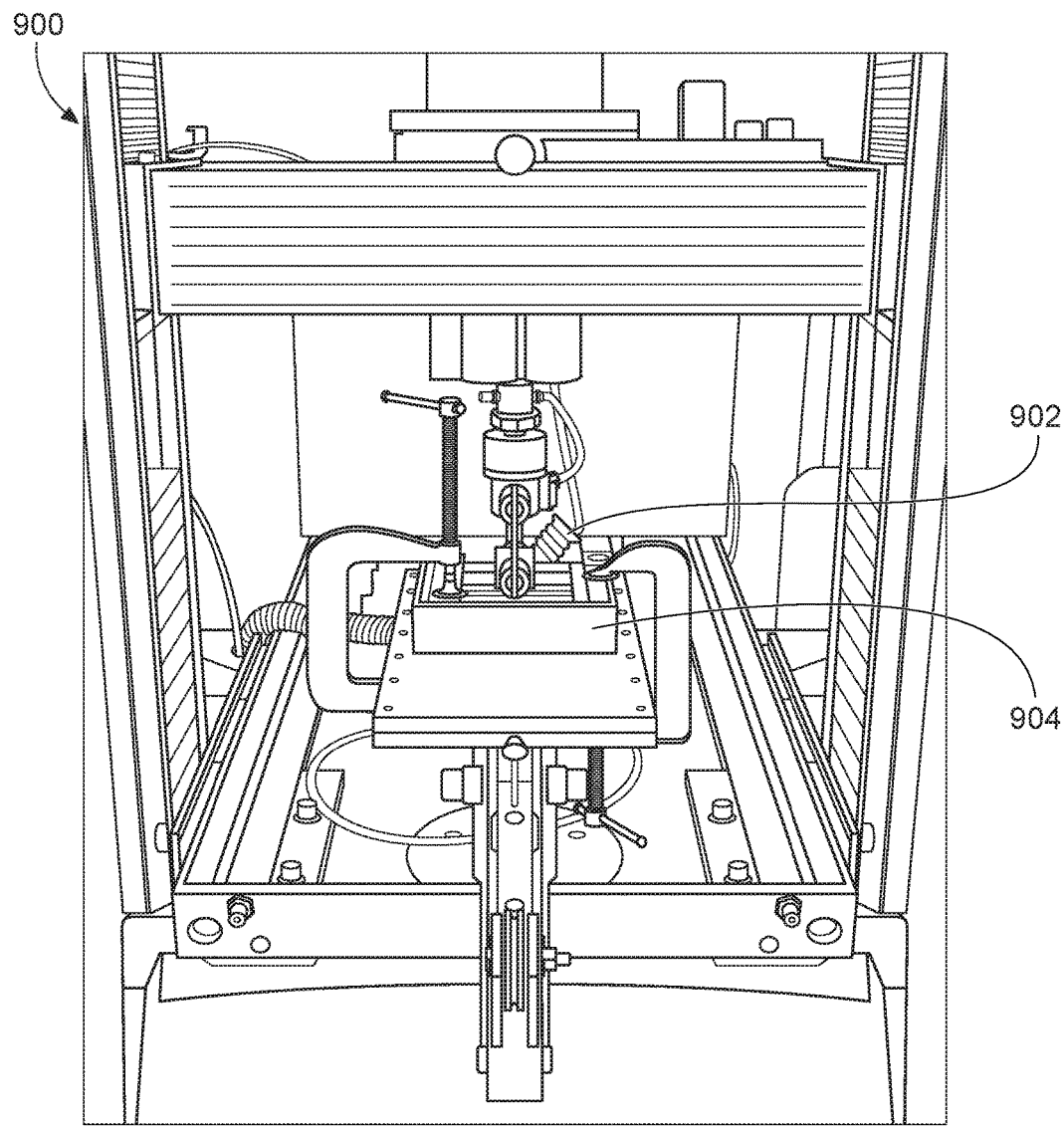
FIG. 27 is a perspective view of a peel test apparatus according to one embodiment illustrated and described herein.
Figure 28A:
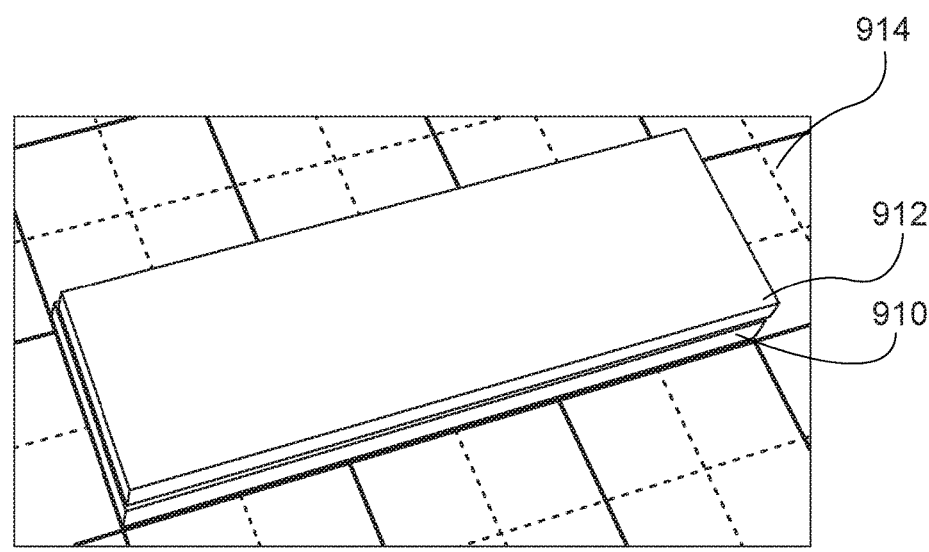
FIG. 28A is a perspective view of a combined rectangular bar according to one embodiment illustrated and described herein.
Figure 28B:
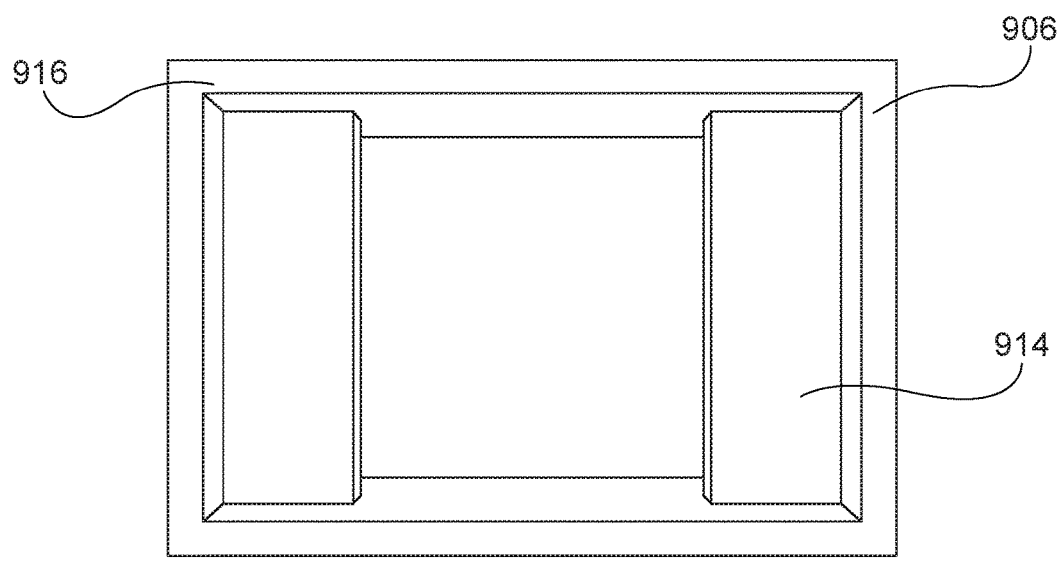
FIG. 28B is a top view of a first assembly step of a strip support apparatus according to one embodiment illustrated and described herein.
Figure 28C:
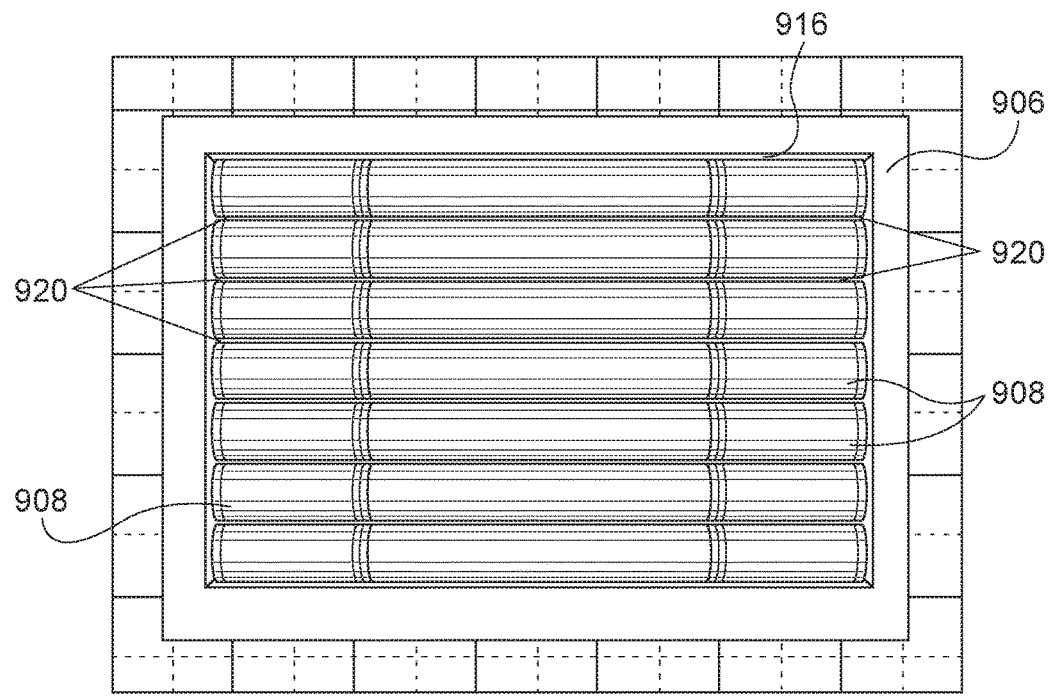
FIG. 28C is a top view of a second assembly step of a strip support apparatus according to one embodiment illustrated and described herein.
Figure 28D:
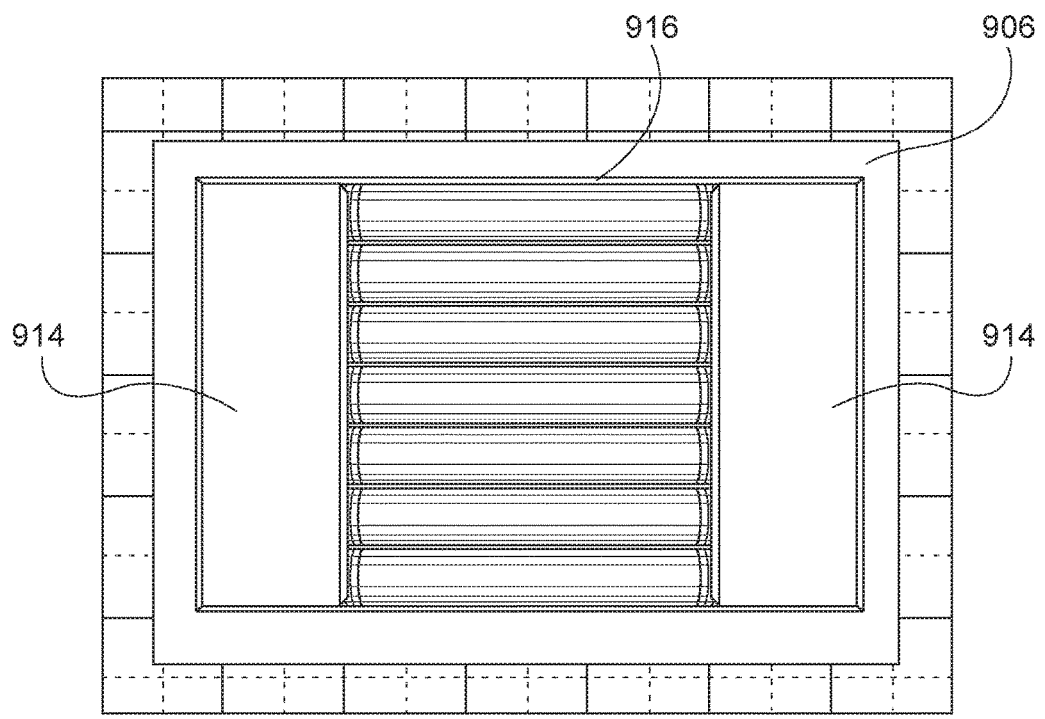
FIG. 28D is a top view of a third assembly step of a strip support apparatus according to one embodiment illustrated and described herein.
Figure 28E:
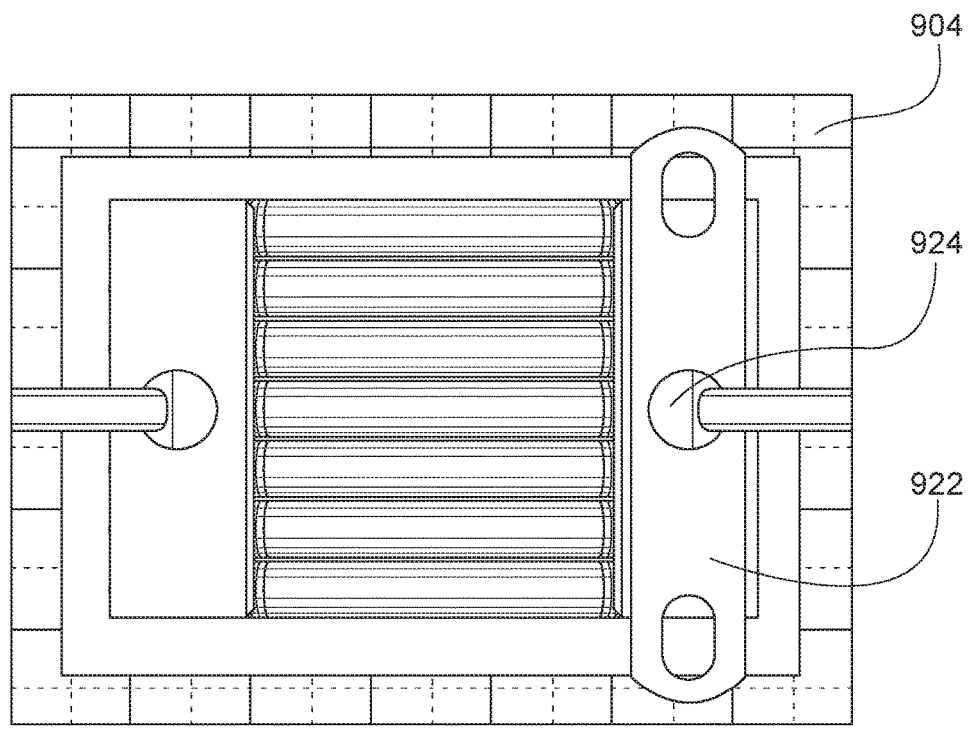
FIG. 28E is a top view of a fourth assembly step of a strip support apparatus according to one embodiment illustrated and described herein.

Strip Removal Test
The Strip Removal Test is described as follows:
Equipment
  Instron Tester Model 5565 and Instron Bluehill software version 1.9. The tester and software are available from Instron Worldwide, Norwood, Mass.
  500 Newton load cell
  90 degree Constant Angle Peel Fixture available from Instron Worldwide, Norwood, Mass.
  Strip support apparatus designed to mimic teeth/mouth.
  Ruler.
  Balance.
  Tweezers and razor blade.
  Sample collection pan.
Test Procedure
  The method for generating the peel test data for Tables 8 and 9 is ASTM standard test method D 3330 Method F—Standardized 90 degree angle peel test for pressure sensitive adhesive, as further described below, with the following modifications: Test Speed is 15.0 mm/sec; and Specimen width is 6.0 mm.
  Obtain a teeth whitening strip product.
  FIG. 27 illustrates a peel test apparatus (Instron Tester Model 5565) and assembly according to ASTM standard test method D 3330 Method F used to measure peel force. The peel test apparatus 900 includes a 90 degree Constant Angle Peel Fixture 902 and a strip support apparatus 904 to mount a teeth whitening strip to in order to run a peel test.
  Strip support apparatus 904 includes the following: a rectangular Teflon box with the dimensions 1.4"×3.5"×5" (outer) and 1"×3.1"×4.7" (inner); seven glass rods having a length of 4.6" and a cut view oval shape 0.29" (thickness), 0.54" (wide), and 0.25" (flat surface); four rectangular plexiglass bars with dimension of 0.29"×1"×3"; four rectangular silicone rubber bars with dimension of 0.19"×1"×3"; one rectangular cellulose compressed sponge with the dimension of 0.05"×2.7"×3.1", available from Loew Cornell; sixteen spacers having 0.02" thickness; two silicone rubber strips having dimension of 0.06"×1"×3"; one silicone rubber strip with a dimension of 0.06"×0.8"×4.5"; two metal bars with dimension of 0.09"×0.75"×3.75"; and a pair of C clamps.
  FIGS. 28A-E illustrate the assembly steps of strip support apparatus 904 as follows: adhere each of the four rectangular plexiglass bars 910 to the four rectangular silicone rectangular bars 912 to form a combined rectangular bar 914 having the dimension 0.48"×1"×3", as shown in FIG. 28A; place two of the combined rectangular bars 914 into the short sides of the Teflon box 906, plexiglass side facing down, as shown in FIG. 28B; place the 0.06"×0.8"×4.5" silicone strip 916 between one edge of the box and the two combined rectangular bars 914, as shown in FIG. 28B; place the sponge in the box between the two combined rectangular bars 914; place the seven glass rods 908 on top of the combined rectangular bars in the box, as shown in FIG. 28C; place all sixteen of the spacers 920 in between the glass rods 908 and between the box and the glass rods 908 such that eight spacers are used on the left side of the box and eight spacers are used on the right side of the box, as shown in FIG. 28C; place the other two combined rectangular bars 914 on top of the glass rods, silicone rubber side facing down and align the top rectangular bars 914 with the bottom rectangular bars, s shown in FIG. 28D; place one 0.06"×1"×3"

silicone rubber strip on top of each combined rectangular bar 914; place one metal bar 922 on top or each silicone rubber strip; and place a C clamp 924 on each side of the box and on top of each metal bar 922, as shown in FIG. 28E.

Once the strip support apparatus 904 is assembled, clamp the apparatus 904 onto the 90 degree Constant Angle Peel Fixture 902.

Inject 50 ml of distilled water into the strip support apparatus 904. Remove excess water with a paper towel making sure there is water between the glass rods and the top of the glass rods remain moistened.

Figure 29:
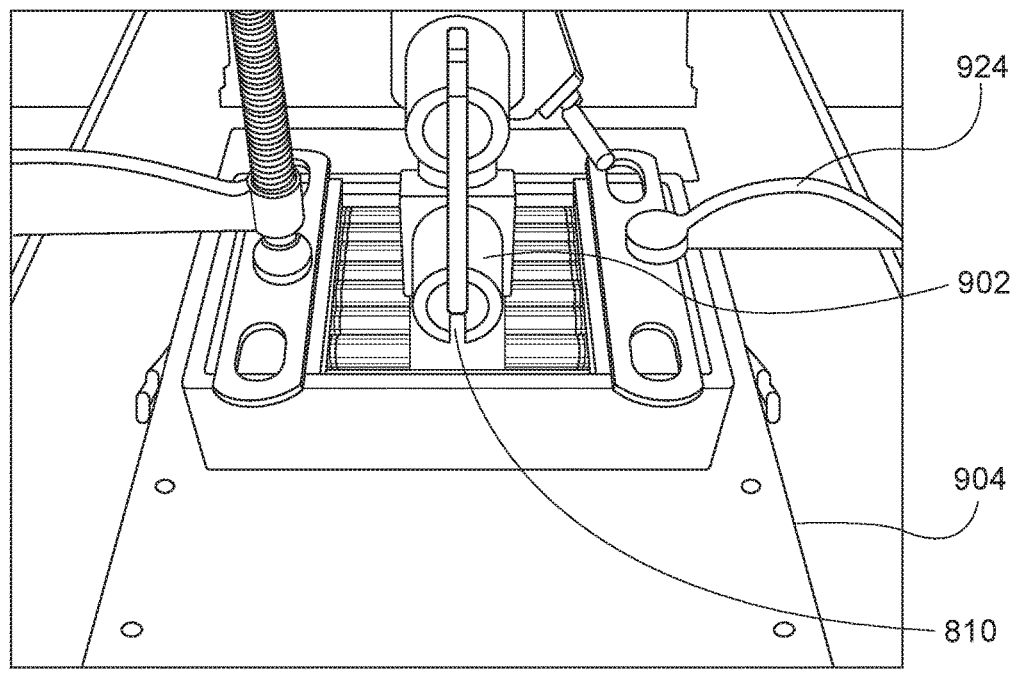
FIG. 29 is a perspective view is a view of the peel test apparatus and strip support apparatus prior to running a peel test according to one embodiment illustrated and described herein.

Cut a teeth whitening strip product to 6 mm wide and adhere 50 mm of the sample onto the glass rods by applying pressure using fingers to make sure that the sample is adhered to the glass rods. Attach one end of the sample to Instron clamp and zero the gauge and force, as shown in FIG. 29.

Figure 30:
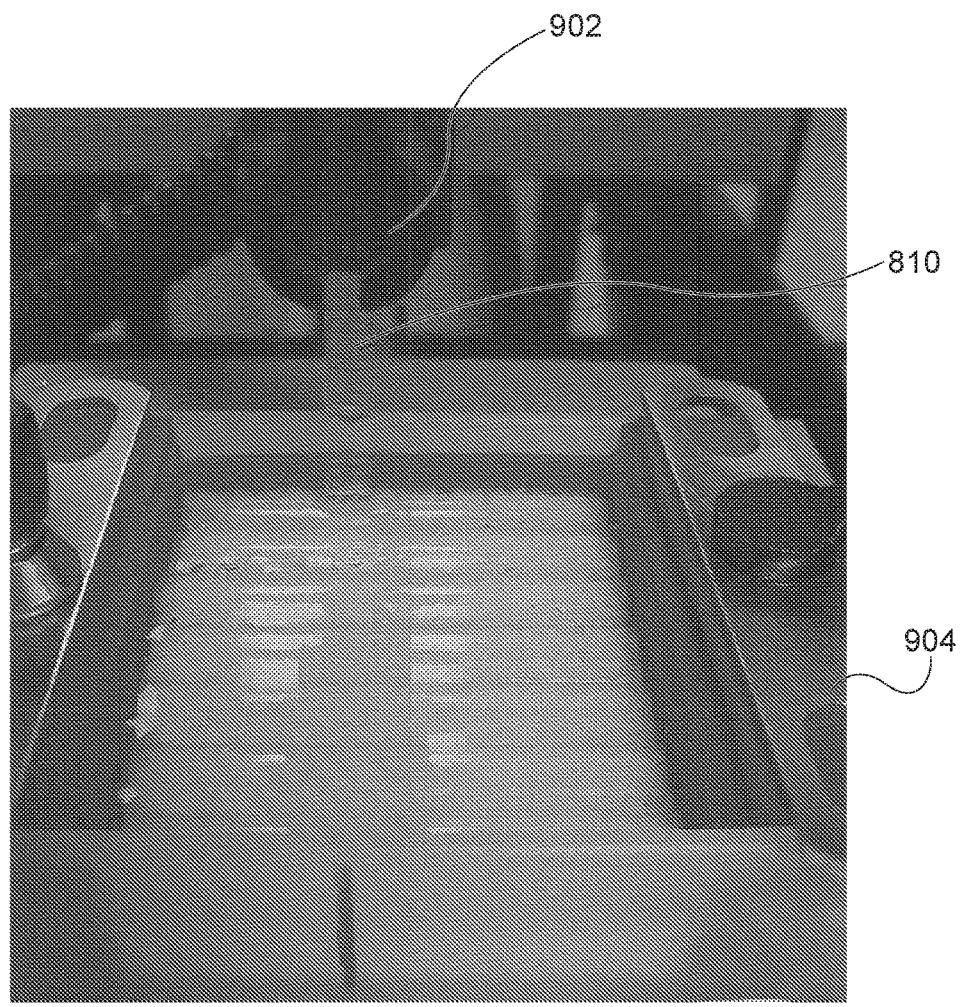
FIG. 30 is a perspective view is a view of the peel test apparatus and strip support apparatus during a peel test according to one embodiment illustrated and described herein.

Start the initial peel test and collect peel force data, as shown in FIG. 30.

Once the initial peel test is complete (3 samples for each Example product in Tables 8 and 9), the test is repeated for each Example product with the following modifications:
  30 min soak—after the sample product is attached to the Instron clamp and the gauge and force are zeroed, use a syringe to spread 5 ml distilled water onto the glass rods; let the sample product soak in the water for 30 minutes; perform peel test and collect peel force data.
  60 min soak—after the sample product is attached to the Instron clamp and onto the glass rods; let the sample product soak in the water for 60 minutes; perform peel test and collect peel force data.

Each example product in Tables 8 and 9 is measured 3 times for each peel test (initial, 30 min, 60 min) and the reported values are aggregated to calculate an average.

After each peel test (initial, 30 min soak, 60 min soak) is performed, the amount of sample material left on the strip support apparatus is determined. First, the length of the gel layer and the length of the backing layer remaining on the glass rods is measured using a ruler. The sample is cut at the intersection of the sample and the glass rods. Weigh tweezers, razor blade and collection pan using a balance. Record the weight and tare the balance. Using the razor blade and tweezers, scrape the sample material left on the glass rods into the collection pan. Once finished, again weigh the tweezer, razor blade and collection pan. Record the weight. 3 samples are measured in this manner for each example product in Table 8 and the reported values are aggregated to calculate an average.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stretchable tooth whitening treatment product, comprising:
   a) a stretchable elastic-like film backing layer, having a transverse axis and having an average thickness of from about 0.1 mil to about 5.0 mil, the film including a blend of:
      i from about 50% to about 90%, by weight of the film, of high-density polyethylene; and
      ii from about 10% to about 50%, by weight of the film, of linear low-density polyethylene; and
   b) an oral care composition disposed on the film, the oral care composition including:
      i from about 50% to about 99.9%, by weight of the composition, of an adhesive polymer; and
      ii from about 0.1% to about 50%, by weight of the composition, of a teeth whitening active;
   said film backing layer including a strainable network having a first region and a second region, the first region providing a first, elastic-like resistive force to an applied axial elongation, and the second region providing a second distinctive resistive force to further applied axial elongation, thereby providing at least two stages of resistive forces in use; and
   wherein said film has a flexural stiffness of less than 4 grams/cm and a Poisson lateral contraction less than 0.8 when said film is subjected to about 25% elongation, or a Poisson lateral contraction less than about 1.0 when subjected to about 50% elongation;
   wherein said second region includes a plurality of raised rib-like elements, said elements having a major axis which is substantially parallel to said transverse axis.

2. A stretchable tooth whitening treatment product according to claim 1 wherein the teeth whitening active is selected from the group consisting of peroxides, metal chlorites, perborates, percarbonates, peroxyacids, and combination thereof.

3. A stretchable tooth whitening treatment product according to claim 1 wherein the teeth whitening active is selected from hydrogen peroxide, calcium peroxide, carbamide peroxide, and mixtures thereof.

4. A stretchable tooth whitening treatment product according to claim 1 wherein the teeth whitening composition comprises an active selected from the group consisting of peroxides, metal chlorites, perborates, percarbonates, peroxyacids, and combinations there; and wherein said composition comprises carboxypolymethylene as an adhesive polymer.

* * * * *